(12) United States Patent  
Wiley et al.

(10) Patent No.: US 9,079,004 B2  
(45) Date of Patent: Jul. 14, 2015

(54) OVERMOLDED ACCESS PORT INCLUDING ANCHORING AND IDENTIFICATION FEATURES

(75) Inventors: Martha Wiley, Salt Lake City, UT (US); Jodie L. Noyce, Salt Lake City, UT (US); David M. Cise, Herriman, UT (US); William R. Barron, Riverton, UT (US); Kelly J. Christian, Draper, UT (US); Amir Orome, Sandy, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/917,323

(22) Filed: Nov. 1, 2010

(65) Prior Publication Data

US 2011/0118677 A1    May 19, 2011

Related U.S. Application Data

(60) Provisional application No. 61/262,126, filed on Nov. 17, 2009.

(51) Int. Cl.  
  *A61M 39/02* (2006.01)  
  *A61M 39/00* (2006.01)

(52) U.S. Cl.  
  CPC ... *A61M 39/0208* (2013.01); *A61M 2039/0081* (2013.01); *A61M 2039/0223* (2013.01); *A61M 2039/0238* (2013.01); *Y10T 29/49826* (2015.01)

(58) Field of Classification Search  
  CPC .................. A61M 39/0208; A61M 2039/0081; A61M 2039/0223; A61M 2039/0238  
  USPC ............ 604/116, 175, 288.01–288.04, 890.1, 604/891.1  
  See application file for complete search history.

(56) References Cited

U.S. PATENT DOCUMENTS

| 445,896 A | 2/1891 | Kinsman |
| 546,440 A | 9/1895 | Tufts |

(Continued)

FOREIGN PATENT DOCUMENTS

| AU | 2008299945 A1 | 3/2009 |
| CA | 2663853 A1 | 4/2008 |

(Continued)

OTHER PUBLICATIONS

AngioDynamics, Smart Port Guidelines for Health Care Providers, 1996.

(Continued)

*Primary Examiner* — Kami A Bosworth  
(74) *Attorney, Agent, or Firm* — Rutan & Tucker, LLP

(57) ABSTRACT

An access port for providing subcutaneous access to a patient is disclosed. In one embodiment, the port includes an internal body defining a fluid cavity that is accessible via a septum. A compliant outer cover including silicone is disposed about at least a portion of the body. A flange is included with the port body and is covered by the outer cover. The flange radially extends about a perimeter of the port body proximate the septum so as to impede penetration of a needle substantially into the outer cover in instances where the needle misses the septum. The flange can further include both an anchoring feature for securing the outer cover to the port body and an identification feature observable via x-ray imaging technology for conveying information indicative of at least one attribute of the access port. The outer cover provides a suitable surface for application of an antimicrobial/antithrombotic coating.

24 Claims, 16 Drawing Sheets

(56) References Cited

U.S. PATENT DOCUMENTS

| | | |
|---|---|---|
| 574,387 A | 1/1897 | Buckler |
| 611,357 A | 9/1898 | Dembinski |
| 966,696 A | 8/1910 | Merrill |
| D44,302 S | 7/1913 | Director |
| 1,713,267 A | 5/1929 | Crowley |
| 2,029,553 A | 2/1936 | Bartischi et al. |
| D130,852 S | 12/1941 | Rothschild |
| 2,433,480 A | 12/1947 | Rendich |
| 2,891,689 A | 6/1959 | Gould |
| D198,453 S | 6/1964 | Weichselbaum |
| 3,159,175 A | 12/1964 | Macmillan |
| 3,211,431 A | 10/1965 | Meysembourg et al. |
| 3,293,663 A | 12/1966 | Cronin |
| 3,341,417 A | 9/1967 | Sinaiko |
| 3,477,438 A | 11/1969 | Allen et al. |
| 3,518,428 A | 6/1970 | Ring |
| 3,525,357 A | 8/1970 | Koreski |
| 3,529,633 A | 9/1970 | Vailancourt |
| 3,540,670 A | 11/1970 | Rissberger |
| 3,541,438 A | 11/1970 | Nelsen et al. |
| 3,643,358 A | 2/1972 | Morderosian |
| D223,340 S | 4/1972 | Diedrich |
| 3,669,323 A | 6/1972 | Harker et al. |
| 3,674,183 A | 7/1972 | Venable et al. |
| 3,811,466 A | 5/1974 | Ohringer |
| 3,829,904 A | 8/1974 | Ling et al. |
| 3,831,549 A | 8/1974 | Parsons |
| 3,831,583 A | 8/1974 | Edmunds, Jr. et al. |
| 3,840,009 A | 10/1974 | Michaels et al. |
| 3,853,127 A | 12/1974 | Spademan |
| 3,891,997 A | 7/1975 | Herbert |
| 3,915,162 A | 10/1975 | Miller |
| 3,919,724 A | 11/1975 | Sanders et al. |
| 3,922,726 A | 12/1975 | Trentani et al. |
| 3,951,147 A | 4/1976 | Tucker et al. |
| 3,955,594 A | 5/1976 | Snow |
| 3,971,376 A | 7/1976 | Wichterle |
| 4,027,391 A | 6/1977 | Samis |
| 4,035,653 A | 7/1977 | Karasko |
| 4,121,108 A | 10/1978 | Manor |
| 4,123,806 A | 11/1978 | Amstutz et al. |
| 4,143,853 A | 3/1979 | Abramson |
| 4,168,586 A | 9/1979 | Samis |
| 4,181,132 A | 1/1980 | Parks |
| 4,190,040 A | 2/1980 | Schulte |
| 4,190,057 A | 2/1980 | Hill et al. |
| 4,194,122 A | 3/1980 | Mitchell et al. |
| 4,196,731 A | 4/1980 | Laurin et al. |
| 4,202,349 A | 5/1980 | Jones |
| 4,222,374 A | 9/1980 | Sampson et al. |
| 4,233,964 A | 11/1980 | Jefferts et al. |
| 4,274,006 A | 6/1981 | Caine |
| D263,335 S | 3/1982 | Bujan |
| 4,349,498 A | 9/1982 | Ellis et al. |
| 4,361,153 A | 11/1982 | Slocum et al. |
| 4,405,305 A | 9/1983 | Stephen et al. |
| 4,406,567 A | 9/1983 | Samis |
| 4,425,119 A | 1/1984 | Berglund |
| 4,445,896 A | 5/1984 | Gianturco |
| 4,447,237 A | 5/1984 | Frisch et al. |
| 4,450,592 A | 5/1984 | Niederer et al. |
| 4,450,985 A | 5/1984 | Beard |
| 4,456,011 A | 6/1984 | Warnecke |
| 4,469,483 A | 9/1984 | Becker et al. |
| 4,479,798 A | 10/1984 | Parks |
| 4,494,545 A | 1/1985 | Slocum et al. |
| 4,506,676 A | 3/1985 | Duska |
| 4,529,635 A | 7/1985 | Sheldon |
| 4,543,088 A | 9/1985 | Bootman et al. |
| 4,549,879 A | 10/1985 | Groshong et al. |
| 4,559,043 A | 12/1985 | Whitehouse et al. |
| 4,559,046 A | 12/1985 | Groshong et al. |
| 4,560,375 A | 12/1985 | Schulte et al. |
| 4,569,675 A | 2/1986 | Prosl et al. |
| 4,571,749 A | 2/1986 | Fischell |
| 4,576,595 A | 3/1986 | Aas et al. |
| 4,610,665 A | 9/1986 | Matsumoto et al. |
| 4,612,877 A | 9/1986 | Hayes et al. |
| 4,626,244 A | 12/1986 | Reinicke |
| 4,627,844 A | 12/1986 | Schmitt |
| 4,634,427 A | 1/1987 | Hannula et al. |
| 4,636,194 A | 1/1987 | Schulte et al. |
| 4,636,213 A | 1/1987 | Pakiam |
| 4,645,495 A | 2/1987 | Vaillancourt |
| 4,653,508 A | 3/1987 | Cosman |
| 4,655,765 A | 4/1987 | Swift |
| 4,657,024 A | 4/1987 | Coneys |
| 4,662,652 A | 5/1987 | Hargis |
| 4,668,221 A | 5/1987 | Luther |
| 4,671,796 A | 6/1987 | Groshong et al. |
| 4,673,394 A | 6/1987 | Fenton, Jr. et al. |
| 4,681,560 A | 7/1987 | Schulte et al. |
| 4,684,365 A | 8/1987 | Reinicke |
| 4,685,447 A | 8/1987 | Iversen et al. |
| 4,685,905 A | 8/1987 | Jeanneret nee Aab |
| 4,692,146 A | 9/1987 | Hilger |
| 4,695,273 A | 9/1987 | Brown |
| 4,697,595 A | 10/1987 | Breyer et al. |
| 4,701,166 A | 10/1987 | Groshong et al. |
| 4,704,103 A | 11/1987 | Stober et al. |
| 4,707,389 A | 11/1987 | Ward |
| 4,710,167 A | 12/1987 | Lazorthes |
| 4,710,174 A | 12/1987 | Moden et al. |
| 4,718,894 A | 1/1988 | Lazorthes |
| 4,723,947 A | 2/1988 | Konopka |
| 4,728,894 A | 3/1988 | Yoda et al. |
| 4,743,231 A | 5/1988 | Kay et al. |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | McIntyre et al. |
| 4,767,410 A | 8/1988 | Moden et al. |
| 4,772,270 A | 9/1988 | Wiita et al. |
| 4,772,276 A | 9/1988 | Wiita et al. |
| 4,773,552 A | 9/1988 | Boege et al. |
| 4,778,452 A | 10/1988 | Moden et al. |
| 4,781,680 A | 11/1988 | Redmond et al. |
| 4,781,685 A | 11/1988 | Lehmann et al. |
| 4,781,695 A | 11/1988 | Dalton |
| 4,784,646 A | 11/1988 | Feingold |
| 4,802,885 A | 2/1989 | Weeks et al. |
| 4,804,054 A | 2/1989 | Howson et al. |
| 4,820,273 A | 4/1989 | Reinicke |
| 4,822,341 A | 4/1989 | Colone |
| 4,840,615 A | 6/1989 | Hancock et al. |
| 4,848,346 A | 7/1989 | Crawford |
| 4,857,053 A | 8/1989 | Dalton |
| 4,861,341 A | 8/1989 | Woodburn |
| 4,863,470 A | 9/1989 | Carter |
| 4,886,501 A | 12/1989 | Johnston et al. |
| 4,886,502 A | 12/1989 | Poirier et al. |
| 4,892,518 A | 1/1990 | Cupp et al. |
| 4,897,081 A | 1/1990 | Poirier et al. |
| 4,904,241 A | 2/1990 | Bark |
| 4,905,709 A | 3/1990 | Bieganski et al. |
| 4,908,029 A | 3/1990 | Bark et al. |
| 4,909,250 A | 3/1990 | Smith |
| 4,915,690 A | 4/1990 | Cone et al. |
| 4,928,298 A | 5/1990 | Tanaka |
| 4,929,236 A | 5/1990 | Sampson |
| 4,955,861 A | 9/1990 | Enegren et al. |
| 4,961,267 A | 10/1990 | Herzog |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 5,002,735 A | 3/1991 | Alberhasky et al. |
| 5,006,115 A | 4/1991 | McDonald |
| 5,009,391 A | 4/1991 | Steigerwald |
| 5,009,644 A | 4/1991 | McDonald |
| 5,013,298 A | 5/1991 | Moden et al. |
| 5,041,098 A | 8/1991 | Loiterman et al. |
| 5,044,955 A | 9/1991 | Jagmin |
| 5,045,060 A | 9/1991 | Melsky et al. |

(56) References Cited

U.S. PATENT DOCUMENTS

| | | |
|---|---|---|
| 5,045,064 A | 9/1991 | Idriss |
| 5,053,013 A | 10/1991 | Ensminger et al. |
| 5,059,186 A | 10/1991 | Yamamoto et al. |
| 5,069,206 A | 12/1991 | Crosbie |
| 5,084,015 A | 1/1992 | Moriuchi |
| 5,085,216 A | 2/1992 | Henley, Jr. et al. |
| 5,090,066 A | 2/1992 | Schoepe et al. |
| 5,092,849 A | 3/1992 | Sampson |
| 5,108,317 A | 4/1992 | Beinhaur et al. |
| 5,108,375 A | 4/1992 | Harrison et al. |
| 5,108,377 A | 4/1992 | Cone et al. |
| 5,112,301 A | 5/1992 | Fenton, Jr. et al. |
| 5,112,303 A | 5/1992 | Pudenz et al. |
| 5,129,891 A | 7/1992 | Young |
| 5,137,529 A | 8/1992 | Watson et al. |
| 5,147,483 A | 9/1992 | Melsky et al. |
| 5,152,753 A | 10/1992 | Laguette et al. |
| 5,156,600 A | 10/1992 | Young |
| 5,158,547 A | 10/1992 | Doan et al. |
| 5,167,629 A | 12/1992 | Vertenstein et al. |
| 5,167,633 A | 12/1992 | Mann et al. |
| 5,167,638 A | 12/1992 | Felix et al. |
| 5,169,393 A | 12/1992 | Moorehead et al. |
| 5,171,228 A | 12/1992 | McDonald |
| 5,176,653 A | 1/1993 | Metals |
| 5,176,662 A | 1/1993 | Bartholomew et al. |
| 5,178,612 A | 1/1993 | Fenton, Jr. |
| 5,180,365 A | 1/1993 | Ensminger et al. |
| 5,185,003 A | 2/1993 | Brethauer |
| 5,189,690 A | 2/1993 | Samuel |
| 5,193,106 A | 3/1993 | DeSena |
| 5,195,122 A | 3/1993 | Fabian |
| 5,195,123 A | 3/1993 | Clement |
| 5,201,715 A | 4/1993 | Masters |
| 5,201,722 A | 4/1993 | Moorehead et al. |
| 5,203,771 A | 4/1993 | Melker et al. |
| 5,203,777 A | 4/1993 | Lee |
| 5,205,834 A | 4/1993 | Moorehead et al. |
| 5,207,644 A | 5/1993 | Strecker |
| 5,213,574 A | 5/1993 | Tucker |
| 5,215,537 A | 6/1993 | Lynn et al. |
| 5,222,499 A | 6/1993 | Allen et al. |
| D337,637 S | 7/1993 | Tucker |
| 5,224,938 A | 7/1993 | Fenton, Jr. |
| 5,242,415 A | 9/1993 | Kantrowitz et al. |
| 5,246,462 A | 9/1993 | Bekki et al. |
| 5,249,598 A | 10/1993 | Schmidt |
| 5,263,930 A | 11/1993 | Ensminger |
| D342,134 S | 12/1993 | Mongeon |
| 5,281,199 A | 1/1994 | Ensminger et al. |
| 5,281,205 A | 1/1994 | McPherson |
| 5,290,263 A | 3/1994 | Wigness et al. |
| 5,295,658 A | 3/1994 | Atkinson et al. |
| 5,299,253 A | 3/1994 | Wessels |
| 5,300,048 A | 4/1994 | Drewes, Jr. et al. |
| 5,309,863 A | 5/1994 | Leeb, Jr. |
| 5,312,337 A | 5/1994 | Flaherty et al. |
| 5,318,545 A | 6/1994 | Tucker |
| 5,320,100 A | 6/1994 | Herweck et al. |
| 5,328,480 A | 7/1994 | Melker et al. |
| 5,332,398 A | 7/1994 | Miller et al. |
| 5,336,194 A | 8/1994 | Polaschegg et al. |
| 5,338,398 A | 8/1994 | Szwejkowski et al. |
| 5,350,360 A | 9/1994 | Ensminger et al. |
| 5,352,204 A | 10/1994 | Ensminger |
| 5,356,381 A | 10/1994 | Ensminger et al. |
| 5,360,407 A | 11/1994 | Leonard et al. |
| 5,383,223 A | 1/1995 | Inokuchi |
| 5,383,233 A | 1/1995 | Russell |
| 5,383,585 A | 1/1995 | Weiss |
| 5,383,858 A | 1/1995 | Reilly et al. |
| D355,240 S | 2/1995 | Gladfelter et al. |
| 5,387,192 A | 2/1995 | Glantz et al. |
| 5,394,457 A | 2/1995 | Leibinger et al. |
| 5,395,324 A | 3/1995 | Hinrichs et al. |
| 5,396,925 A | 3/1995 | Poli |
| 5,397,329 A | 3/1995 | Allen |
| 5,399,168 A | 3/1995 | Wadsworth, Jr. et al. |
| 5,405,402 A | 4/1995 | Dye et al. |
| 5,417,565 A | 5/1995 | Long |
| 5,417,656 A | 5/1995 | Ensminger et al. |
| 5,421,814 A | 6/1995 | Geary |
| 5,423,334 A | 6/1995 | Jordan |
| 5,425,762 A | 6/1995 | Muller |
| 5,453,097 A | 9/1995 | Paradis |
| 5,456,698 A | 10/1995 | Byland et al. |
| 5,476,451 A | 12/1995 | Ensminger et al. |
| 5,476,460 A | 12/1995 | Montalvo |
| 5,476,880 A | 12/1995 | Cooke et al. |
| 5,484,402 A | 1/1996 | Saravia et al. |
| 5,503,630 A | 4/1996 | Ensminger et al. |
| 5,507,813 A | 4/1996 | Dowd et al. |
| 5,509,805 A | 4/1996 | Jagmin |
| 5,513,637 A | 5/1996 | Twiss et al. |
| 5,514,103 A | 5/1996 | Srisathapat et al. |
| 5,520,632 A | 5/1996 | Leveen et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,527,307 A | 6/1996 | Srisathapat et al. |
| 5,531,684 A | 7/1996 | Ensminger et al. |
| 5,542,923 A | 8/1996 | Ensminger et al. |
| 5,545,143 A | 8/1996 | Fischell |
| 5,554,117 A | 9/1996 | Ensminger et al. |
| 5,556,381 A | 9/1996 | Ensminger et al. |
| 5,558,641 A | 9/1996 | Glantz et al. |
| 5,558,829 A | 9/1996 | Petrick |
| 5,562,617 A | 10/1996 | Finch, Jr. et al. |
| 5,562,618 A | 10/1996 | Cai et al. |
| 5,575,770 A | 11/1996 | Melsky et al. |
| 5,593,028 A | 1/1997 | Haber et al. |
| 5,593,434 A | 1/1997 | Williams |
| 5,607,393 A | 3/1997 | Ensminger et al. |
| 5,607,407 A | 3/1997 | Tolkoff et al. |
| 5,613,945 A | 3/1997 | Cai et al. |
| 5,620,419 A | 4/1997 | Lui et al. |
| 5,632,729 A | 5/1997 | Cai et al. |
| 5,637,102 A | 6/1997 | Tolkoff et al. |
| 5,638,832 A | 6/1997 | Singer et al. |
| 5,647,855 A | 7/1997 | Trooskin |
| RE35,601 E | 9/1997 | Eckenhoff |
| 5,662,600 A | 9/1997 | Watson et al. |
| 5,662,612 A | 9/1997 | Niehoff |
| 5,662,616 A | 9/1997 | Bousquet |
| 5,676,146 A | 10/1997 | Scarborough |
| 5,695,490 A | 12/1997 | Flaherty et al. |
| 5,702,128 A | 12/1997 | Maxim et al. |
| 5,702,363 A | 12/1997 | Flaherty |
| 5,704,915 A | 1/1998 | Melsky et al. |
| 5,707,357 A | 1/1998 | Mikhail et al. |
| 5,709,668 A | 1/1998 | Wacks |
| 5,713,844 A | 2/1998 | Peyman |
| 5,713,858 A | 2/1998 | Heruth et al. |
| 5,713,859 A | 2/1998 | Finch, Jr. et al. |
| 5,718,382 A | 2/1998 | Jaeger |
| 5,718,682 A | 2/1998 | Tucker |
| 5,725,507 A | 3/1998 | Petrick |
| 5,733,336 A | 3/1998 | Neuenfeldt et al. |
| 5,733,400 A | 3/1998 | Gore et al. |
| 5,741,228 A | 4/1998 | Lambrecht et al. |
| 5,743,873 A | 4/1998 | Cai et al. |
| 5,743,891 A | 4/1998 | Tolkoff et al. |
| 5,746,460 A | 5/1998 | Marohl et al. |
| 5,755,780 A | 5/1998 | Finch, Jr. et al. |
| 5,758,667 A | 6/1998 | Slettenmark |
| 5,769,823 A | 6/1998 | Otto |
| 5,773,552 A | 6/1998 | Hutchings et al. |
| 5,776,188 A | 7/1998 | Shepherd et al. |
| 5,792,104 A | 8/1998 | Speckman et al. |
| 5,792,116 A | 8/1998 | Berg et al. |
| 5,792,123 A | 8/1998 | Ensminger |
| 5,797,886 A | 8/1998 | Roth et al. |
| 5,810,789 A | 9/1998 | Powers et al. |
| 5,814,016 A | 9/1998 | Valley et al. |

(56) References Cited

U.S. PATENT DOCUMENTS

| | | | |
|---|---|---|---|
| 5,824,071 A | 10/1998 | Nelson et al. |
| 5,830,172 A | 11/1998 | Leveen et al. |
| 5,833,654 A | 11/1998 | Powers et al. |
| 5,835,563 A | 11/1998 | Navab et al. |
| 5,836,935 A | 11/1998 | Ashton et al. |
| 5,840,063 A | 11/1998 | Flaherty |
| 5,843,069 A | 12/1998 | Butler et al. |
| 5,848,989 A | 12/1998 | Villani |
| 5,853,394 A | 12/1998 | Tolkoff et al. |
| 5,868,702 A | 2/1999 | Stevens et al. |
| 5,879,322 A | 3/1999 | Lattin et al. |
| 5,882,341 A | 3/1999 | Bousquet |
| 5,882,353 A | 3/1999 | VanBeek et al. |
| 5,895,424 A | 4/1999 | Steele, Sr. et al. |
| 5,897,528 A | 4/1999 | Schultz |
| 5,899,856 A | 5/1999 | Schoendorfer et al. |
| 5,904,934 A * | 5/1999 | Maruyama et al. ........... 424/473 |
| 5,906,592 A | 5/1999 | Kriesel et al. |
| 5,906,596 A | 5/1999 | Tallarida |
| 5,908,413 A | 6/1999 | Lange et al. |
| 5,908,414 A | 6/1999 | Otto et al. |
| 5,911,706 A | 6/1999 | Estabrook et al. |
| 5,913,998 A | 6/1999 | Butler et al. |
| 5,916,263 A | 6/1999 | Goicoechea et al. |
| 5,919,160 A | 7/1999 | Sanfilippo, II |
| 5,925,017 A | 7/1999 | Kriesel et al. |
| 5,925,030 A | 7/1999 | Gross et al. |
| 5,927,345 A | 7/1999 | Samson |
| 5,928,197 A | 7/1999 | Niehoff |
| 5,928,744 A | 7/1999 | Heilmann et al. |
| 5,931,829 A | 8/1999 | Burbank et al. |
| 5,941,856 A | 8/1999 | Kovacs et al. |
| 5,944,023 A | 8/1999 | Johnson et al. |
| 5,944,688 A | 8/1999 | Lois |
| 5,944,698 A | 8/1999 | Fischer et al. |
| 5,944,712 A | 8/1999 | Frassica et al. |
| D413,672 S | 9/1999 | Fogarty |
| 5,947,953 A | 9/1999 | Ash et al. |
| 5,951,512 A | 9/1999 | Dalton |
| 5,951,522 A | 9/1999 | Rosato et al. |
| 5,951,929 A | 9/1999 | Wilson |
| 5,954,687 A | 9/1999 | Baudino |
| 5,954,691 A | 9/1999 | Prosl |
| 5,957,890 A | 9/1999 | Mann et al. |
| 5,961,497 A | 10/1999 | Larkin |
| 5,968,011 A | 10/1999 | Larsen et al. |
| 5,970,162 A | 10/1999 | Kawashima |
| 5,989,216 A | 11/1999 | Johnson et al. |
| 5,989,239 A | 11/1999 | Finch et al. |
| 5,989,641 A | 11/1999 | Oulie |
| 5,997,524 A | 12/1999 | Burbank et al. |
| 6,007,516 A | 12/1999 | Burbank et al. |
| 6,013,051 A | 1/2000 | Nelson |
| 6,013,058 A | 1/2000 | Prosl et al. |
| 6,017,331 A | 1/2000 | Watts et al. |
| 6,022,335 A | 2/2000 | Ramadan |
| 6,033,389 A | 3/2000 | Cornish |
| 6,039,712 A | 3/2000 | Fogarty et al. |
| 6,056,717 A | 5/2000 | Finch et al. |
| 6,077,756 A | 6/2000 | Lin et al. |
| 6,086,555 A | 7/2000 | Eliasen et al. |
| 6,090,066 A | 7/2000 | Schnell |
| 6,099,508 A | 8/2000 | Bousquet |
| 6,102,884 A | 8/2000 | Squitieri |
| 6,113,572 A | 9/2000 | Gailey et al. |
| 6,120,492 A | 9/2000 | Finch et al. |
| 6,152,909 A | 11/2000 | Bagaoisan et al. |
| 6,161,033 A | 12/2000 | Kuhn |
| 6,171,198 B1 | 1/2001 | Lizama Troncoso et al. |
| 6,171,298 B1 | 1/2001 | Matsuura et al. |
| 6,186,982 B1 | 2/2001 | Gross et al. |
| 6,190,352 B1 | 2/2001 | Haarala et al. |
| 6,193,684 B1 | 2/2001 | Burbank et al. |
| 6,198,807 B1 | 3/2001 | DeSena |
| 6,200,338 B1 | 3/2001 | Solomon et al. |
| 6,203,570 B1 | 3/2001 | Baeke |
| 6,210,366 B1 | 4/2001 | Sanfilippo, II |
| 6,213,973 B1 | 4/2001 | Eliasen et al. |
| 6,228,088 B1 | 5/2001 | Miller et al. |
| 6,251,059 B1 | 6/2001 | Apple et al. |
| D445,175 S | 7/2001 | Bertheas |
| 6,261,259 B1 | 7/2001 | Bell |
| 6,269,148 B1 | 7/2001 | Jessop et al. |
| 6,272,370 B1 | 8/2001 | Gillies et al. |
| 6,287,293 B1 | 9/2001 | Jones et al. |
| 6,290,677 B1 | 9/2001 | Arai et al. |
| 6,305,413 B1 | 10/2001 | Fischer et al. |
| 6,306,124 B1 | 10/2001 | Jones et al. |
| D450,115 S | 11/2001 | Bertheas |
| 6,315,762 B1 | 11/2001 | Recinella et al. |
| 6,332,874 B1 | 12/2001 | Eliasen et al. |
| 6,355,021 B1 | 3/2002 | Nielsen et al. |
| 6,356,782 B1 | 3/2002 | Sirimanne et al. |
| 6,361,557 B1 | 3/2002 | Gittings et al. |
| 6,398,764 B1 | 6/2002 | Finch, Jr. et al. |
| 6,419,680 B1 | 7/2002 | Cosman et al. |
| 6,450,937 B1 | 9/2002 | Mercereau et al. |
| 6,473,638 B2 | 10/2002 | Ferek-Petric |
| 6,475,516 B2 | 11/2002 | DiCosmo et al. |
| 6,478,783 B1 | 11/2002 | Moorehead |
| 6,482,217 B1 | 11/2002 | Pintor et al. |
| 6,494,867 B1 | 12/2002 | Elver et al. |
| 6,497,062 B1 | 12/2002 | Koopman et al. |
| 6,500,155 B2 | 12/2002 | Sasso |
| 6,503,228 B1 | 1/2003 | Li et al. |
| 6,527,754 B1 | 3/2003 | Tallarida et al. |
| 6,537,255 B1 | 3/2003 | Raines |
| RE38,074 E | 4/2003 | Recinella et al. |
| 6,562,023 B1 | 5/2003 | Marrs et al. |
| 6,572,583 B1 | 6/2003 | Olsen et al. |
| 6,582,418 B1 | 6/2003 | Verbeek et al. |
| 6,592,571 B1 | 7/2003 | Verbeek et al. |
| 6,610,031 B1 | 8/2003 | Chin |
| 6,613,002 B1 | 9/2003 | Clark et al. |
| 6,613,662 B2 | 9/2003 | Wark et al. |
| 6,626,936 B2 | 9/2003 | Stinson |
| D480,942 S | 10/2003 | Ishida et al. |
| 6,629,950 B1 | 10/2003 | Levin |
| 6,632,217 B2 | 10/2003 | Harper et al. |
| 6,652,486 B2 | 11/2003 | Bialecki et al. |
| 6,652,503 B1 | 11/2003 | Bradley |
| 6,663,646 B1 | 12/2003 | Shah |
| 6,676,633 B2 | 1/2004 | Smith et al. |
| 6,697,664 B2 | 2/2004 | Kienzle, III et al. |
| 6,705,316 B2 | 3/2004 | Blythe et al. |
| 6,719,721 B1 | 4/2004 | Okazaki et al. |
| 6,719,739 B2 | 4/2004 | Verbeek et al. |
| 6,726,063 B2 | 4/2004 | Stull et al. |
| 6,738,531 B1 | 5/2004 | Funahashi |
| 6,755,842 B2 | 6/2004 | Kanner et al. |
| 6,758,841 B2 | 7/2004 | Haarala et al. |
| 6,767,356 B2 | 7/2004 | Kanner et al. |
| 6,784,783 B2 | 8/2004 | Scoggin et al. |
| 6,808,738 B2 | 10/2004 | DiTizio et al. |
| D498,894 S | 11/2004 | Gould |
| 6,826,257 B2 | 11/2004 | Sayre et al. |
| 6,827,709 B2 | 12/2004 | Fujii |
| 6,852,106 B2 | 2/2005 | Watson et al. |
| 6,856,055 B2 | 2/2005 | Michaels et al. |
| 6,878,136 B2 | 4/2005 | Fleury et al. |
| 6,878,137 B2 | 4/2005 | Benchetrit |
| 6,929,631 B1 | 8/2005 | Brugger et al. |
| 6,949,084 B2 | 9/2005 | Marggi et al. |
| 6,953,453 B2 | 10/2005 | Recinella et al. |
| 6,962,577 B2 | 11/2005 | Tallarida et al. |
| 6,962,580 B2 | 11/2005 | Adams et al. |
| 6,994,315 B2 | 2/2006 | Ryan et al. |
| 6,997,914 B2 | 2/2006 | Smith et al. |
| 7,008,377 B2 | 3/2006 | Beane et al. |
| 7,008,412 B2 | 3/2006 | Maginot |
| 7,016,456 B2 | 3/2006 | Basu et al. |
| 7,018,361 B2 | 3/2006 | Gillespie, Jr. et al. |
| D518,573 S | 4/2006 | French |
| 7,033,335 B2 | 4/2006 | Haarala et al. |

(56) References Cited

U.S. PATENT DOCUMENTS

| | | | |
|---|---|---|---|
| 7,033,339 B1 | 4/2006 | Lynn | |
| 7,044,942 B2 | 5/2006 | Jolly et al. | |
| 7,056,316 B1 | 6/2006 | Burbank et al. | |
| 7,070,591 B2 | 7/2006 | Adams et al. | |
| 7,072,704 B2 | 7/2006 | Bucholz | |
| 7,074,232 B2 | 7/2006 | Kanner et al. | |
| 7,076,305 B2 | 7/2006 | Imran et al. | |
| 7,083,593 B2 | 8/2006 | Stultz | |
| 7,108,686 B2 | 9/2006 | Burke et al. | |
| 7,123,690 B1 | 10/2006 | Brown et al. | |
| 7,124,570 B2 | 10/2006 | Blatter et al. | |
| 7,127,040 B2 | 10/2006 | Sayre et al. | |
| 7,131,962 B1 | 11/2006 | Estabrook et al. | |
| 7,140,769 B2 | 11/2006 | Kay | |
| 7,186,236 B2 | 3/2007 | Gibson et al. | |
| 7,191,011 B2 | 3/2007 | Cantlon | |
| 7,198,631 B2 | 4/2007 | Kanner et al. | |
| 7,214,207 B2 | 5/2007 | Lynch et al. | |
| 7,214,215 B2 | 5/2007 | Heinzerling et al. | |
| 7,223,257 B2 | 5/2007 | Shubayev et al. | |
| 7,229,417 B2 | 6/2007 | Foerster et al. | |
| 7,232,429 B2 | 6/2007 | Moreci | |
| 7,235,067 B2 | 6/2007 | Morris et al. | |
| D546,440 S | 7/2007 | Burnside | |
| 7,242,982 B2 | 7/2007 | Singhal et al. | |
| 7,248,668 B2 | 7/2007 | Galkin | |
| 7,252,469 B2 | 8/2007 | Zaluzec et al. | |
| 7,252,649 B2 | 8/2007 | Sherry | |
| 7,261,705 B2 | 8/2007 | Edoga et al. | |
| D550,355 S | 9/2007 | Racz et al. | |
| D554,253 S | 10/2007 | Kornerup | |
| 7,275,682 B2 | 10/2007 | Excoffier et al. | |
| 7,276,075 B1 | 10/2007 | Callas et al. | |
| D556,153 S | 11/2007 | Burnside | |
| 7,306,579 B2 | 12/2007 | Fujii | |
| 7,311,702 B2 | 12/2007 | Tallarida et al. | |
| 7,318,816 B2 | 1/2008 | Bobroff et al. | |
| 7,318,818 B2 | 1/2008 | Yashiro et al. | |
| 7,322,953 B2 | 1/2008 | Redinger | |
| D562,442 S | 2/2008 | Blateri | |
| D562,443 S | 2/2008 | Zinn et al. | |
| 7,331,130 B2 | 2/2008 | Schweikert | |
| 7,331,948 B2 | 2/2008 | Skarda | |
| 7,333,013 B2 | 2/2008 | Berger | |
| D564,449 S | 3/2008 | Dewberry | |
| 7,347,838 B2 | 3/2008 | Kulli | |
| 7,347,843 B2 | 3/2008 | Adams et al. | |
| 7,351,233 B2 | 4/2008 | Parks | |
| 7,377,915 B2 | 5/2008 | Rasmussen et al. | |
| D574,950 S | 8/2008 | Zawacki et al. | |
| 7,413,564 B2 | 8/2008 | Morris et al. | |
| D578,203 S | 10/2008 | Bizup | |
| 7,445,614 B2 | 11/2008 | Bunodiere et al. | |
| D582,032 S | 12/2008 | Bizup et al. | |
| 7,465,847 B2 | 12/2008 | Fabian | |
| 7,485,148 B2 | 2/2009 | Wozencroft et al. | |
| 7,497,850 B2 | 3/2009 | Halili | |
| D590,499 S | 4/2009 | Chesnin | |
| 7,552,853 B2 | 6/2009 | Mas et al. | |
| 7,553,298 B2 | 6/2009 | Hunt et al. | |
| D595,892 S | 7/2009 | Smith et al. | |
| 7,563,025 B2 | 7/2009 | Kay | |
| 7,628,776 B2 | 12/2009 | Gibson et al. | |
| 7,658,196 B2 | 2/2010 | Ferreri et al. | |
| D612,479 S | 3/2010 | Zawacki et al. | |
| D613,394 S | 4/2010 | Linden | |
| 7,713,251 B2 | 5/2010 | Tallarida et al. | |
| 7,722,580 B2 | 5/2010 | Dicarlo et al. | |
| D619,242 S | 7/2010 | Zinn et al. | |
| 7,785,302 B2 | 8/2010 | Powers | |
| 7,803,143 B2 | 9/2010 | Tallarida et al. | |
| 7,806,888 B2 | 10/2010 | Frassica | |
| 7,811,266 B2 | 10/2010 | Eliasen | |
| D629,503 S | 12/2010 | Caffey et al. | |
| 7,846,139 B2 | 12/2010 | Zinn et al. | |
| 7,850,660 B2 | 12/2010 | Uth et al. | |
| 7,862,546 B2 | 1/2011 | Conlon et al. | |
| D634,840 S | 3/2011 | Lombardi, III et al. | |
| 7,909,804 B2 | 3/2011 | Stats | |
| 7,947,022 B2 | 5/2011 | Amin et al. | |
| 7,959,615 B2 | 6/2011 | Stats et al. | |
| 7,972,314 B2 | 7/2011 | Bizup et al. | |
| 8,007,474 B2 | 8/2011 | Uth et al. | |
| 8,021,324 B2 | 9/2011 | Bizup et al. | |
| 8,025,639 B2 | 9/2011 | Powers et al. | |
| 8,029,482 B2 | 10/2011 | Maniar et al. | |
| D650,475 S | 12/2011 | Smith et al. | |
| 8,075,536 B2 | 12/2011 | Gray et al. | |
| 8,092,435 B2 | 1/2012 | Beling et al. | |
| 8,147,455 B2 | 4/2012 | Butts et al. | |
| 8,172,894 B2 | 5/2012 | Schmid et al. | |
| 8,172,896 B2 | 5/2012 | McNamara et al. | |
| 8,177,762 B2 | 5/2012 | Beasley et al. | |
| 8,182,453 B2 | 5/2012 | Eliasen | |
| 8,197,454 B2 * | 6/2012 | Mann et al. | 604/288.04 |
| 8,202,259 B2 | 6/2012 | Evans et al. | |
| 8,257,325 B2 | 9/2012 | Schweikert et al. | |
| D676,955 S | 2/2013 | Orome | |
| 8,366,687 B2 | 2/2013 | Girard et al. | |
| 8,377,034 B2 | 2/2013 | Tallarida et al. | |
| 8,382,723 B2 | 2/2013 | Powers et al. | |
| 8,382,724 B2 | 2/2013 | Maniar et al. | |
| 8,409,153 B2 | 4/2013 | Tallarida et al. | |
| 8,475,417 B2 | 7/2013 | Powers et al. | |
| 8,545,460 B2 | 10/2013 | Beasley et al. | |
| 8,585,663 B2 | 11/2013 | Powers et al. | |
| 8,603,052 B2 | 12/2013 | Powers et al. | |
| 8,608,712 B2 | 12/2013 | Bizup et al. | |
| 8,608,713 B2 | 12/2013 | Beasley et al. | |
| 8,641,676 B2 | 2/2014 | Butts et al. | |
| 8,641,688 B2 | 2/2014 | Powers et al. | |
| 8,805,478 B2 | 8/2014 | Powers et al. | |
| 8,852,160 B2 | 10/2014 | Schweikert et al. | |
| 8,932,271 B2 | 1/2015 | Hamatake et al. | |
| 8,939,947 B2 | 1/2015 | Maniar et al. | |
| 2001/0016717 A1 | 8/2001 | Haarala et al. | |
| 2001/0047165 A1 | 11/2001 | Makower et al. | |
| 2001/0051766 A1 | 12/2001 | Gazdzinski | |
| 2001/0053889 A1 | 12/2001 | Marggi et al. | |
| 2001/0056266 A1 | 12/2001 | Tallarida et al. | |
| 2002/0013557 A1 | 1/2002 | Sherry | |
| 2002/0052576 A1 | 5/2002 | Massengale | |
| 2002/0055715 A1 | 5/2002 | Young et al. | |
| 2002/0095205 A1 | 7/2002 | Edwin et al. | |
| 2002/0121530 A1 | 9/2002 | Socier | |
| 2002/0138068 A1 | 9/2002 | Watson et al. | |
| 2002/0169418 A1 | 11/2002 | Menzi et al. | |
| 2002/0173769 A1 | 11/2002 | Gray et al. | |
| 2002/0173772 A1 | 11/2002 | Olsen | |
| 2002/0183846 A1 | 12/2002 | Kuslich et al. | |
| 2002/0188282 A1 * | 12/2002 | Greenberg | 604/890.1 |
| 2003/0028173 A1 | 2/2003 | Forsberg | |
| 2003/0093029 A1 | 5/2003 | McGuckin et al. | |
| 2003/0109856 A1 | 6/2003 | Sherry | |
| 2003/0130627 A1 | 7/2003 | Smith et al. | |
| 2003/0139812 A1 | 7/2003 | Garcia et al. | |
| 2003/0141477 A1 | 7/2003 | Miller | |
| 2003/0181878 A1 | 9/2003 | Tallarida et al. | |
| 2003/0191452 A1 | 10/2003 | Meglin et al. | |
| 2003/0208184 A1 | 11/2003 | Burke et al. | |
| 2003/0216694 A1 | 11/2003 | Tollini | |
| 2003/0217659 A1 | 11/2003 | Yamamoto et al. | |
| 2004/0002693 A1 | 1/2004 | Bright et al. | |
| 2004/0006316 A1 | 1/2004 | Patton | |
| 2004/0020462 A1 | 2/2004 | Sauler et al. | |
| 2004/0020492 A1 | 2/2004 | Dubrul et al. | |
| 2004/0044306 A1 | 3/2004 | Lynch et al. | |
| 2004/0054352 A1 | 3/2004 | Adams et al. | |
| 2004/0056266 A1 | 3/2004 | Suh et al. | |
| 2004/0064110 A1 | 4/2004 | Forsell | |
| 2004/0073196 A1 | 4/2004 | Adams et al. | |
| 2004/0078000 A1 | 4/2004 | Borchard et al. | |
| 2004/0086568 A1 | 5/2004 | Ditizio et al. | |
| 2004/0087877 A1 | 5/2004 | Besz et al. | |

(56) References Cited

U.S. PATENT DOCUMENTS

| | | |
|---|---|---|
| 2004/0087885 A1 | 5/2004 | Kawano et al. |
| 2004/0106878 A1 | 6/2004 | Skujins et al. |
| 2004/0106891 A1 | 6/2004 | Langan et al. |
| 2004/0106942 A1 | 6/2004 | Taylor et al. |
| 2004/0133173 A1 | 7/2004 | Edoga et al. |
| 2004/0156472 A1 | 8/2004 | Galkin |
| 2004/0157952 A1 | 8/2004 | Soffiati et al. |
| 2004/0158207 A1 | 8/2004 | Hunn et al. |
| 2004/0167543 A1 | 8/2004 | Mazzocchi et al. |
| 2004/0176743 A1 | 9/2004 | Morris et al. |
| 2004/0186444 A1 | 9/2004 | Daly et al. |
| 2004/0199129 A1 | 10/2004 | DiMatteo |
| 2004/0199220 A1 | 10/2004 | Cantlon |
| 2004/0204692 A1 | 10/2004 | Eliasen |
| 2004/0204759 A1 | 10/2004 | Blom et al. |
| 2004/0225254 A1 | 11/2004 | Tanaka et al. |
| 2004/0254536 A1 | 12/2004 | Conlon et al. |
| 2004/0254537 A1 | 12/2004 | Conlon et al. |
| 2005/0010176 A1 | 1/2005 | Dikeman et al. |
| 2005/0010286 A1 | 1/2005 | Vijay |
| 2005/0027234 A1 | 2/2005 | Waggoner et al. |
| 2005/0027261 A1 | 2/2005 | Weaver et al. |
| 2005/0038390 A1 | 2/2005 | Fago et al. |
| 2005/0049553 A1 | 3/2005 | Triplett et al. |
| 2005/0070875 A1 | 3/2005 | Kulessa |
| 2005/0075614 A1 | 4/2005 | Bunodiere et al. |
| 2005/0080401 A1 | 4/2005 | Peavey |
| 2005/0085778 A1 | 4/2005 | Parks |
| 2005/0113806 A1 | 5/2005 | De Carvalho et al. |
| 2005/0124980 A1 | 6/2005 | Sanders |
| 2005/0131352 A1 | 6/2005 | Conlon et al. |
| 2005/0148866 A1 | 7/2005 | Gunderson |
| 2005/0148869 A1 | 7/2005 | Masuda |
| 2005/0148956 A1 | 7/2005 | Conlon et al. |
| 2005/0148957 A1 | 7/2005 | Girard et al. |
| 2005/0152841 A1 | 7/2005 | Sayre et al. |
| 2005/0171502 A1 | 8/2005 | Daly et al. |
| 2005/0182857 A1 | 8/2005 | Kong |
| 2005/0209573 A1 | 9/2005 | Brugger et al. |
| 2005/0215874 A1 | 9/2005 | Wang et al. |
| 2005/0241203 A1 | 11/2005 | Lizotte et al. |
| 2005/0256451 A1 | 11/2005 | Adams et al. |
| 2005/0256500 A1 | 11/2005 | Fujii |
| 2005/0277899 A1 | 12/2005 | Conlon et al. |
| 2005/0283119 A1 | 12/2005 | Uth et al. |
| 2006/0009788 A1 | 1/2006 | Freeman et al. |
| 2006/0017341 A1 | 1/2006 | Hahn et al. |
| 2006/0084929 A1 | 4/2006 | Eliasen |
| 2006/0089619 A1 | 4/2006 | Ginggen |
| 2006/0100592 A1 | 5/2006 | Eliasen |
| 2006/0116648 A1 | 6/2006 | Hamatake |
| 2006/0171980 A1 | 8/2006 | Helmus et al. |
| 2006/0173410 A1 | 8/2006 | Moberg et al. |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0184142 A1 | 8/2006 | Schon et al. |
| 2006/0217359 A1 | 9/2006 | Wentworth et al. |
| 2006/0217659 A1 | 9/2006 | Patton |
| 2006/0217668 A1 | 9/2006 | Schulze et al. |
| 2006/0224128 A1 | 10/2006 | Lurvey et al. |
| 2006/0224129 A1 | 10/2006 | Beasley et al. |
| 2006/0224235 A1 | 10/2006 | Rucker |
| 2006/0241465 A1 | 10/2006 | Huennekens et al. |
| 2006/0247584 A1 | 11/2006 | Sheetz et al. |
| 2006/0253076 A1 | 11/2006 | Butts et al. |
| 2006/0264897 A1* | 11/2006 | Lobl et al. .................. 604/506 |
| 2006/0264898 A1 | 11/2006 | Beasley et al. |
| 2006/0271012 A1 | 11/2006 | Canaud et al. |
| 2007/0003603 A1 | 1/2007 | Karandikar et al. |
| 2007/0007839 A1 | 1/2007 | Lin |
| 2007/0010881 A1* | 1/2007 | Soye et al. .................. 623/6.34 |
| 2007/0016162 A1 | 1/2007 | Burbank et al. |
| 2007/0049806 A1 | 3/2007 | Adams et al. |
| 2007/0049876 A1 | 3/2007 | Patton |
| 2007/0055290 A1 | 3/2007 | Lober |
| 2007/0073250 A1 | 3/2007 | Schneiter |
| 2007/0078391 A1 | 4/2007 | Wortley et al. |
| 2007/0078416 A1 | 4/2007 | Eliasen |
| 2007/0078432 A1 | 4/2007 | Halseth et al. |
| 2007/0083111 A1 | 4/2007 | Hossack et al. |
| 2007/0083156 A1 | 4/2007 | Muto et al. |
| 2007/0100302 A1 | 5/2007 | Dicarlo et al. |
| 2007/0112332 A1 | 5/2007 | Harding et al. |
| 2007/0120683 A1 | 5/2007 | Flippen et al. |
| 2007/0123831 A1 | 5/2007 | Haindl et al. |
| 2007/0135775 A1 | 6/2007 | Edoga et al. |
| 2007/0149920 A1 | 6/2007 | Michels et al. |
| 2007/0149921 A1 | 6/2007 | Michels et al. |
| 2007/0149947 A1 | 6/2007 | Byrum |
| 2007/0161958 A1 | 7/2007 | Glenn |
| 2007/0179456 A1 | 8/2007 | Glenn |
| 2007/0185462 A1 | 8/2007 | Byrum |
| 2007/0191773 A1 | 8/2007 | Wojcik |
| 2007/0207335 A1 | 9/2007 | Karandikar et al. |
| 2007/0208313 A1 | 9/2007 | Conlon et al. |
| 2007/0219510 A1 | 9/2007 | Zinn et al. |
| 2007/0233017 A1 | 10/2007 | Zinn et al. |
| 2007/0233018 A1 | 10/2007 | Bizup et al. |
| 2007/0255226 A1 | 11/2007 | Tennican et al. |
| 2007/0255234 A1 | 11/2007 | Haase et al. |
| 2007/0270691 A1 | 11/2007 | Bailey et al. |
| 2007/0270770 A1 | 11/2007 | Bizup |
| 2007/0276344 A1 | 11/2007 | Bizup et al. |
| 2007/0276355 A1 | 11/2007 | Nielsen et al. |
| 2007/0282308 A1 | 12/2007 | Bell |
| 2007/0293800 A1 | 12/2007 | McMaken et al. |
| 2007/0299408 A1 | 12/2007 | Alferness et al. |
| 2008/0004642 A1 | 1/2008 | Birk et al. |
| 2008/0008654 A1 | 1/2008 | Clarke et al. |
| 2008/0015701 A1 | 1/2008 | Garcia et al. |
| 2008/0039820 A1 | 2/2008 | Sommers et al. |
| 2008/0048855 A1 | 2/2008 | Berger |
| 2008/0108949 A1 | 5/2008 | Beasley et al. |
| 2008/0114308 A1 | 5/2008 | di Palma et al. |
| 2008/0133265 A1 | 6/2008 | Silkaitis et al. |
| 2008/0137923 A1 | 6/2008 | Spahn |
| 2008/0138387 A1 | 6/2008 | Machiraju |
| 2008/0140025 A1 | 6/2008 | Sheetz et al. |
| 2008/0208236 A1 | 8/2008 | Hobbs et al. |
| 2008/0281279 A1 | 11/2008 | Hoendervoogt et al. |
| 2008/0319398 A1 | 12/2008 | Bizup |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0035582 A1 | 2/2009 | Nakatani et al. |
| 2009/0118683 A1 | 5/2009 | Hanson et al. |
| 2009/0156928 A1 | 6/2009 | Evans et al. |
| 2009/0204072 A1 | 8/2009 | Amin et al. |
| 2009/0204074 A1 | 8/2009 | Powers et al. |
| 2009/0216216 A1 | 8/2009 | Powers et al. |
| 2009/0221976 A1 | 9/2009 | Linden |
| 2009/0227862 A1 | 9/2009 | Smith et al. |
| 2009/0227951 A1 | 9/2009 | Powers et al. |
| 2009/0227964 A1 | 9/2009 | DiCarlo et al. |
| 2009/0264901 A1 | 10/2009 | Franklin et al. |
| 2009/0322541 A1 | 12/2009 | Jones et al. |
| 2010/0010339 A1 | 1/2010 | Smith et al. |
| 2010/0042073 A1 | 2/2010 | Oster et al. |
| 2010/0063451 A1 | 3/2010 | Gray et al. |
| 2010/0069743 A1 | 3/2010 | Sheetz et al. |
| 2010/0106094 A1 | 4/2010 | Fisher et al. |
| 2010/0121283 A1 | 5/2010 | Hamatake et al. |
| 2010/0211026 A2 | 8/2010 | Sheetz et al. |
| 2010/0268165 A1 | 10/2010 | Maniar et al. |
| 2010/0268174 A1 | 10/2010 | Steinke et al. |
| 2011/0021922 A1 | 1/2011 | Berard-Anderson et al. |
| 2011/0092921 A1 | 4/2011 | Beling et al. |
| 2011/0098662 A1 | 4/2011 | Zinn |
| 2011/0098663 A1 | 4/2011 | Zinn |
| 2011/0183712 A1 | 7/2011 | Eckstein et al. |
| 2011/0213700 A1 | 9/2011 | Sant'Anselmo |

(56) References Cited

U.S. PATENT DOCUMENTS

| | | |
|---|---|---|
| 2011/0257609 A1 | 10/2011 | Bizup et al. |
| 2011/0264058 A1 | 10/2011 | Linden et al. |
| 2011/0271856 A1 | 11/2011 | Fisher et al. |
| 2011/0275930 A1 | 11/2011 | Jho et al. |
| 2011/0276015 A1 | 11/2011 | Powers et al. |
| 2011/0288502 A1 | 11/2011 | Hibdon et al. |
| 2011/0288503 A1 | 11/2011 | Magalich et al. |
| 2011/0311337 A1 | 12/2011 | Amin et al. |
| 2012/0018073 A1 | 1/2012 | Maniar et al. |
| 2012/0059250 A1 | 3/2012 | Gray et al. |
| 2012/0065622 A1 | 3/2012 | Cornish et al. |
| 2012/0078201 A1 | 3/2012 | Mikami |
| 2012/0078202 A1 | 3/2012 | Beling et al. |
| 2012/0191071 A1 | 7/2012 | Butts et al. |
| 2012/0226244 A1 | 9/2012 | Beasley et al. |
| 2012/0259296 A1 | 10/2012 | Sheetz et al. |
| 2012/0283560 A1 | 11/2012 | Schweikert et al. |
| 2012/0302969 A1 | 11/2012 | Wiley et al. |
| 2013/0165773 A1 | 6/2013 | Powers et al. |
| 2013/0172733 A1 | 7/2013 | Maniar et al. |
| 2013/0218103 A1 | 8/2013 | Tallarida et al. |
| 2013/0225990 A1 | 8/2013 | Powers et al. |
| 2013/0225991 A1 | 8/2013 | Powers |
| 2013/0245574 A1 | 9/2013 | Powers et al. |
| 2013/0338494 A1 | 12/2013 | Wiley et al. |
| 2014/0081219 A1 | 3/2014 | Powers et al. |
| 2014/0100534 A1 | 4/2014 | Beasley et al. |
| 2014/0107619 A1 | 4/2014 | Butts et al. |
| 2014/0330118 A1 | 11/2014 | Powers et al. |
| 2015/0025478 A1 | 1/2015 | Hibdon et al. |

FOREIGN PATENT DOCUMENTS

| | | |
|---|---|---|
| CA | 2692142 A1 | 12/2008 |
| CA | 2693972 A1 | 1/2009 |
| CN | 102421469 A | 4/2012 |
| CN | 102612343 A | 7/2012 |
| DE | 3618390 C1 | 11/1987 |
| DE | 3720414 A1 | 12/1987 |
| DE | 42 25 524 A1 | 2/1994 |
| DE | 29512576 U1 | 10/1995 |
| DE | 10346470 A1 | 5/2005 |
| EP | 0128525 A2 | 12/1984 |
| EP | 0134745 A1 | 3/1985 |
| EP | 0343910 A2 | 11/1989 |
| EP | 0366814 A1 | 5/1990 |
| EP | 0239244 | 9/1991 |
| EP | 0534782 A1 | 3/1993 |
| EP | 0619101 A1 | 10/1994 |
| EP | 1238682 A2 | 9/2002 |
| EP | 1635899 A2 | 3/2006 |
| EP | 2006019101 A2 | 12/2006 |
| EP | 1858565 A1 | 11/2007 |
| EP | 1874393 A1 | 1/2008 |
| EP | 1896117 A2 | 3/2008 |
| EP | 1998842 A2 | 12/2008 |
| EP | 2004272 A2 | 12/2008 |
| EP | 2018209 A2 | 1/2009 |
| EP | 2081634 A1 | 7/2009 |
| EP | 2164559 A1 | 3/2010 |
| EP | 2167182 A1 | 3/2010 |
| EP | 2180915 A1 | 5/2010 |
| EP | 2190517 A1 | 6/2010 |
| EP | 2308547 A2 | 4/2011 |
| EP | 2320974 A1 | 5/2011 |
| EP | 2324878 A2 | 5/2011 |
| EP | 2324879 A2 | 5/2011 |
| EP | 2324880 A2 | 5/2011 |
| EP | 2365838 A1 | 9/2011 |
| EP | 2571563 A1 | 3/2013 |
| EP | 2601999 A1 | 6/2013 |
| EP | 2324879 B1 | 1/2014 |
| FR | 1509165 A | 1/1968 |
| FR | 2508008 A1 | 12/1982 |
| FR | 2809315 A1 | 11/2001 |
| GB | 178998 A | 5/1922 |
| GB | 749942 A | 6/1956 |
| GB | 966137 A | 8/1964 |
| GB | 1559140 A | 1/1980 |
| GB | 2102398 A | 2/1983 |
| GB | 2191701 A | 12/1987 |
| GB | 2350352 A | 11/2000 |
| JP | 62155857 A | 7/1987 |
| JP | 62281966 A | 12/1987 |
| JP | 6296633 A | 10/1994 |
| JP | 2000-079168 A | 3/2000 |
| JP | 2002500076 A | 1/2002 |
| JP | 2003-510136 A | 3/2003 |
| JP | 2004-350937 A | 12/2004 |
| JP | 2006025948 A | 2/2006 |
| JP | 2012-523284 A | 10/2012 |
| JP | 2013-510652 | 3/2013 |
| JP | 2013-526376 A | 6/2013 |
| WO | 8600213 A1 | 1/1986 |
| WO | 8911309 A1 | 11/1989 |
| WO | 9001958 A1 | 3/1990 |
| WO | 9206732 A1 | 4/1992 |
| WO | 9300945 A1 | 1/1993 |
| WO | 9305730 A1 | 4/1993 |
| WO | 9308986 A1 | 5/1993 |
| WO | 9405351 A1 | 3/1994 |
| WO | 9515194 | 6/1995 |
| WO | 9516480 A1 | 6/1995 |
| WO | 9701370 A1 | 1/1997 |
| WO | 9706845 A1 | 2/1997 |
| WO | 9711726 A1 | 4/1997 |
| WO | 9723255 A1 | 7/1997 |
| WO | 9726931 A1 | 7/1997 |
| WO | 9817337 A1 | 4/1998 |
| WO | 9818506 A1 | 5/1998 |
| WO | 9831417 A2 | 7/1998 |
| WO | 9934859 A1 | 7/1999 |
| WO | 9938553 A1 | 8/1999 |
| WO | 9942166 A1 | 8/1999 |
| WO | 0012171 A1 | 3/2000 |
| WO | 0016844 A1 | 3/2000 |
| WO | 0033901 A1 | 6/2000 |
| WO | 0123023 A1 | 4/2001 |
| WO | 0160444 A1 | 8/2001 |
| WO | 0195813 | 12/2001 |
| WO | 0247549 A1 | 6/2002 |
| WO | 03084832 A1 | 10/2003 |
| WO | 03090509 A2 | 11/2003 |
| WO | 2004004800 A2 | 1/2004 |
| WO | 2004028611 A1 | 4/2004 |
| WO | 2004071555 A2 | 8/2004 |
| WO | 2004091434 A2 | 10/2004 |
| WO | 2005037055 A2 | 4/2005 |
| WO | 2005068009 A1 | 7/2005 |
| WO | 2006078915 A2 | 7/2006 |
| WO | 2006096686 A1 | 9/2006 |
| WO | 2006116438 A2 | 11/2006 |
| WO | 2006116613 A1 | 11/2006 |
| WO | 2006130133 A1 | 12/2006 |
| WO | 2006134100 A1 | 12/2006 |
| WO | 2007041471 A2 | 4/2007 |
| WO | 2007079024 A2 | 7/2007 |
| WO | 2007092210 A1 | 8/2007 |
| WO | 2007094898 A2 | 8/2007 |
| WO | 2007098771 A2 | 9/2007 |
| WO | 2007109164 A2 | 9/2007 |
| WO | 2007126645 A2 | 11/2007 |
| WO | 2007136538 A2 | 11/2007 |
| WO | 2008008126 A2 | 1/2008 |
| WO | 2008019236 A1 | 2/2008 |
| WO | 2008048361 A1 | 4/2008 |
| WO | 2008062173 A1 | 5/2008 |
| WO | 2008063226 A2 | 5/2008 |
| WO | 2008147760 A1 | 12/2008 |
| WO | 2008157763 A1 | 12/2008 |
| WO | 2009002839 A1 | 12/2008 |
| WO | 2009012385 A1 | 1/2009 |
| WO | 2009012395 A1 | 1/2009 |

(56) References Cited

FOREIGN PATENT DOCUMENTS

| WO | 2009035582 A1 | 3/2009 |
|---|---|---|
| WO | 2009046439 A2 | 4/2009 |
| WO | 2009046725 A1 | 4/2009 |
| WO | 2009108669 A1 | 9/2009 |
| WO | 2010030351 A1 | 3/2010 |
| WO | 2010062633 A1 | 6/2010 |
| WO | 2010118144 A1 | 10/2010 |
| WO | 2011046604 A2 | 4/2011 |
| WO | 2011053499 A1 | 5/2011 |
| WO | 2011056619 A1 | 5/2011 |
| WO | 2011062750 A1 | 5/2011 |
| WO | 2011133950 A1 | 10/2011 |
| WO | 2011146649 A1 | 11/2011 |
| WO | 2014031763 A2 | 2/2014 |

OTHER PUBLICATIONS

Bard Access Systems Mar. 21, 1995 Product Release to Market form for "M.R.I. Port with 8 Fr. ChronoFlexÒ Catheter", "M.R.I. Port with 8Fr. ChronoFlex Catheter with Intro-Eze™", "M.R.I. Port with 8. Fr ChronoFlex Catheter and Peel Apart", "M.R.I. Port with 8Fr. ChronoFlex Catheter Demo Kit". Drawings included.
Bard Healthcare Leaflet (2001).
Baxter Guidelines on Port Maintainence (Jun. 2003).
Baxter Healthport® Focus (Oct. 1999).
Baxter Healthport® Venous Systems (Oct. 2002).
Baxter Patient Information, Healthport® System (May 1999).
Baxter Therapy Systems, Baxter Healthport® Jan. 1999.
Biffi, R. et al. "Use of totally implantable central venous access ports for high-dose chemotherapy and peripheral blood stem cell transplantation: results of a monocentre series of 376 patients." Annals of Oncology 15:296-300, 2004.
Biffi, R., et al. "Best Choice of Central Venous Insertion Site for the Prevention of Catheter-Related Complications in Adult Patients Who Need Cancer Therapy: A Randomized Trial." Annals of Oncology, Jan. 29, 2009.
Biffi, Roberto, et al. "A Randomized, Prospective Trial of Central Venous Ports Connected to Standard Open-Ended or Groshong Catheters in Adult Oncology Patients." American Cancer Society, vol. 92, No. 5, pp. 1204-1212, Sep. 1, 2001.
Inamed Health, BioEnterics LAP-BAND "Adjustable Gastric Banding System" Product Brochure, Dec. 2003.
Braun Product Catalog (Aug. 2005).
Cardiovascular and Interventional Radiology, Review Article, "Central Venous Access Catheters: Radiological Management of Complications," by U.K. Teichgraber, B. Gebauer, T. Benter, H.J. Wagner, published online Jul. 31, 2003.
Carlson et al., "Safety Considerations in the Power Injection of Contrast Media Via Central Venous Catheters during Computed Tomographic Examinations," Investigative Radiology, (May 1992) 27: 337-340.
Cook Vital-Port® Product Catalog (2000).
Costa, Nancy, "More Than Skin Deep: An Overview of Iodinated Contrast Media . . . " Journal for the Association for Vascular Access, vol. 8, No. 4, 2003.
Costa, Nancy, "Understanding Contrast Media." Journal of Infusion Nursing, vol. 27, No. 5, Sep./Oct. 2004.
Coyle, Douglas et al, Power Injection of Contrast Media via Peripherally Inserted Central Catheters for CT, J Vasc Interv Radiol, pp. 809-814, vol. 15, 2004.
Deltec Port Systems (Feb. and Apr. 1996).
Department of Health and Human Services, C-Port 510(k) FDA Clearance, Jun. 5, 2003.
EP 06751411 filed Apr. 25, 2006 Office Action dated Aug. 10, 2009.
EP 06751411 filed Apr. 25, 2006 Office Action dated Sep. 2, 2008.
EP 06751411 filed Apr. 25, 2006 Opposition by Aesculap AG dated Oct. 5, 2011.
EP 06751411 filed Apr. 25, 2006 Opposition by Fresenius Kabi Deutschland GmbH dated Oct. 11, 2011.
EP 06751411 filed Apr. 25, 2006 Opposition by pfm medical ag dated Oct. 12, 2011.
EP 06845998 filed Dec. 21, 2006 Office Action dated Mar. 10, 2011.
EP 06845998 filed Dec. 21, 2006 Supplementary Search Report dated Jul. 22, 2010.
EP 99964086 filed Dec. 3, 1999 Office Action dated Dec. 15, 2005.
EP 99964086 filed Dec. 3, 1999 Office Action dated Mar. 1, 2005.
EP 99964086 filed Dec. 3, 1999 Office Action dated Mar. 30, 2005.
Extravasation of Radiologic Contrast, PA-PSRS Patient Safety Advisory, vol. 1 No. 3, Sep. 2004.
Extreme Access™ Bard Access Systems, Inc. Product Brochure, 2003.
Fallscheer, et al., "Injury to the Upper Extremity Cuased by Extravasation of Contrast Medium: A True Emergency." Scandinavian Journal of Plastic and Reconstructive Surgery and Hand Surgery, vol. 41, pp. 26-32, 2007.
Fresenius Brochure on Intraport 1, Intraport II, and Bioport (Nov. 1998).
Gebauer, B. et al., "Contrast Media Power Injection Using Central Venous Port Catheters—Results of an In-Vitro Study," Experimental Radiology 2005: 177: 1417-1423.
Hou, Shaw-Min et al. "Comparisons of Outcomes and Survivals for Two Central Venous Access Port Systems." Journal of Surgical Oncology, 91:61-66, 2005.
Clinical Plastic Products, "Oncology Jet Port Plus Catheter Systems" Instructions for Use, 2011.
Johnson, Kathleen A., "Power Injectable Portal Systems." Journal of Radiology Nursing, vol. 28, Issue 1, Mar. 2009.
JP 2007-558331 filed Mar. 6, 2006 Office Action dated May 17, 2011.
JP 2008-509056 filed Apr. 25, 2006 Office Action dated Jun. 7, 2011.
Kaste et al., "Safe use of power injectors with central and peripheral venous access devices for pediatric CT," Pediatr Radiol (1996) 26: 499-501.
L-CATH® for Ports, Luther Medical Products, Inc., Tustin, California, 2 pages, 1994.
LaMaitre Vascular "Port Implantations: using the OptiLock Implantable Port," product information, available at http://www.lemaitre.com/specs.pop.asp, last accessed Apr. 2003, 14 pages.
LAP-BAND® AP ™ "System with Adjustable Gastric Banding system with OMNIFORM TN Design," Product Brochure, Jul. 2007, 16 pages.
LAP-BAND® System Access Port Fill Guide I, "9.75/10.0 cm LAP-BAND System vs. 11 cm LAP-BAND System: For Product Manufactured Prior to Jul. 2001" BioEnterics Corporation.
Allergan, Inc. LAP-BAND® System Fact Sheet. © 2007.
Leslie et al., "A New Simple Power Injector," Am J Roentgenol 128: 381-384, Mar. 1977.
MedComp "PortCT Technology", display at SIR Conference (Mar. 2006), Toronto, Canada.
U.S. Appl. No. 11/380,621, filed Apr. 27, 2006 Non-Final Office Action dated Jun. 6, 2008.
U.S. Appl. No. 11/725,287, filed Mar. 19, 2007 Non-final Office Action issued on Dec. 3, 2008.
U.S. Appl. No. 11/725,287, filed Mar. 19, 2007 Non-final Office Action issued on Jun. 12, 2009.
U.S. Appl. No. 11/725,287, filed Mar. 19, 2007 Non-final Office Action issued on Mar. 29, 2010.
U.S. Appl. No. 11/937,302, filed Nov. 8, 2007 Final Office Action dated Feb. 11, 2011.
U.S. Appl. No. 11/937,302, filed Nov. 8, 2007 Non-Final Office Action dated Apr. 15, 2011.
U.S. Appl. No. 11/937,302, filed Nov. 8, 2007 Non-Final Office Action dated Sep. 13, 2010.
U.S. Appl. No. 12/023,280, filed Jan. 31, 2008 Final Office Action dated Mar. 9, 2010.
U.S. Appl. No. 12/023,280, filed Jan. 31, 2008 Non-Final Office Action dated Dec. 13, 2010.
U.S. Appl. No. 12/023,280, filed Jan. 31, 2008 Non-Final Office Action dated Jul. 23, 2009.
U.S. Appl. No. 12/023,280, filed Jan. 31, 2008 Non-Final Office Action dated Oct. 5, 2009.
U.S. Appl. No. 12/023,280, filed Jan. 31, 2008 Notice of Allowance dated Mar. 28, 2011.

(56) References Cited

OTHER PUBLICATIONS

U.S. Appl. No. 12/143,377, filed Jun. 20, 2008 Final Office Action mailed Oct. 19, 2009.
U.S. Appl. No. 12/143,377, filed Jun. 20, 2008 Non-final Office Action mailed Apr. 27, 2009.
U.S. Appl. No. 12/175,182, filed Jul. 17, 2008 Non-final Office Action mailed Sep. 3, 2009.
U.S. Appl. No. 12/419,854, filed Apr. 7, 2009 Non-Final Office Action dated Aug. 5, 2011.
U.S. Appl. No. 12/419,957, filed Apr. 7, 2009 Advisory Action dated Feb. 18, 2011.
U.S. Appl. No. 12/419,957, filed Apr. 7, 2009 Final Office Action dated Dec. 7, 2010.
U.S. Appl. No. 12/419,957, filed Apr. 7, 2009 Non-Final Office Action dated Feb. 18, 2010.
U.S. Appl. No. 12/419,957, filed Apr. 7, 2009 Non-Final Office Action dated Jul. 29, 2010.
U.S. Appl. No. 12/419,957, filed Apr. 7, 2009 Non-Final Office Action dated Jun. 30, 2009.
U.S. Appl. No. 12/419,957, filed Apr. 7, 2009 Notice of Allowance dated Mar. 7, 2011.
U.S. Appl. No. 12/420,007, filed Apr. 7, 2009 Final Office Action dated Feb. 18, 2010.
U.S. Appl. No. 12/420,007, filed Apr. 7, 2009 Non-Final Office Action dated Jul. 14, 2009.
U.S. Appl. No. 12/420,028, filed Apr. 7, 2009 Non-Final Office Action dated Jan. 5, 2011.
U.S. Appl. No. 12/420,028, filed Apr. 7, 2009 Notice of Allowance dated Apr. 1, 2011.
U.S. Appl. No. 12/617,981, filed Nov. 13, 2009 Advisory Action dated Sep. 15, 2011.
U.S. Appl. No. 12/617,981, filed Nov. 13, 2009 Final Office Action dated Jun. 21, 2011.
U.S. Appl. No. 12/617,981, filed Nov. 13, 2009 Non-Final Office Action dated Jan. 5, 2011.
U.S. Appl. No. 12/796,133, filed Jun. 8, 2010 Non-Final Office Action dated Feb. 17, 2011.
U.S. Appl. No. 12/796,133, filed Jun. 8, 2010 Notice of Allowance dated Jun. 9, 2011.
U.S. Appl. No. 29/239,163, filed Sep. 27, 2005 entitled Injectable Power Port, listing Eddie K. Burnside as inventor.
U.S. Appl. No. 29/247,954, filed Jul. 21, 2006 entitled Injectable Power Port, listing Eddie K. Burnside as inventor.
U.S. Appl. No. 29/247,954, filed Jul. 21, 2006 Non-Final Office Action dated Apr. 6, 2007.
U.S. Appl. No. 29/247,954, filed Jul. 21, 2006 Notice of Allowability dated Jul. 30, 2007.
U.S. Appl. No. 29/284,454, filed Sep. 7, 2007 titled Implantable Port Device, listing John A. Zawacki and Annmarie Boswell as inventors, in which a Continued Prosecution Application was filed on Jan. 30, 2008.
U.S. Appl. No. 29/284,456, filed Sep. 7, 2007, titled Implantable Port Device, listing John A. Zawacki and Annemarie Boswell as inventors.
Vergara, et al., "Adverse Reactions to Contrast Medica in CT: Effects of Temperature and Ionic Property." Radiology, vol. 199, No. 2, May 1996.
Vogelzang, Robert L., "Power Injection Through Central Venous Catheters: Physiological and Hemodynamic Considerations." The McGaw Medical Center of Northwestern University, Feinberg School of Medicine. Jun. 23, 2004.
Wells, S. "Venous Access in Oncology and Haematology Patients: Part One." Nursing Standard, vol. 22, No. 52, pp. 39-46, Sep. 3, 2008.
Wikipedia, "Port Catheter", Dec. 15, 2011.
Williamson, et al., "Assessing the Adequacy of Peripherally Inserted Central Catheters for Power Injection of Intravenous Contrast Agents for CT." Journal of Computer Assisted Tomography, vol. 6, No. 6, pp. 932-937, 2001.
Sanelli, et al., "Safety and Feasibility of Using a Central Venous Catheter for Rapid Contrast Injection Rates." American Journal of Radiology, vol. 183, pp. 1829-1834, Dec. 2004.

Shah, Tilak M., "Radiopaque Polymer Formulations for Medical Devices." Medical Device and Diagnostic Industry, Mar. 2000.
Smith, Lisa Hartkoph, "Implanted Ports, Computed Tomography, Power Injectors, and Catheter Rupture." Clinical Journal of Oncology Nursing, vol. 12 , No. 5. Oct. 2008.
Soloman, et al., "CIN Strategies: Anticipate, Manage, Prevent." Supplement to Imaging Economics, May 2007.
Statement of Prof. Dr. med. Karl R. Aigner, Oct. 11, 2011.
Steinbach, Barbara G. , Hardt, N. Sisson, Abbitt, Patricia L., Lanier, Linda, Caffee, H. Hollis, "Breast Implants, Common Complications, and Concurrent Breast Disease." RadioGraphics, vol. 13, No. 1, pp. 95-118, 1993.
Sullivan et al. "Radiopaque Markers on Mammary Implants." American Journal of Roentgenology 153(2):428, Aug. 1989.
U.S. Food and Drug Administration, "Guidance for Institutional Review Boards and Clinical Investigators 1998 Update: Medical Devices." Version Sep. 10, 2008.
U.S. Appl. No. 60/658,518, filed Mar. 4, 2005, publicly accessible Oct. 5, 2006.
Urquiola, Javier, et al., "Using Lead Foil as a Radiopaque Marker for Computerized Tomography Imaging When Implant Treatment Planning." The Journal of Prosthetic Dentistry, 1997.
U.S. Appl. No. 10/374,000, filed Feb. 25, 2003 Office Action dated Aug. 28, 2007.
U.S. Appl. No. 10/374,000, filed Feb. 25, 2003 Advisory Action dated Jan. 23, 2007.
U.S. Appl. No. 10/374,000, filed Feb. 25, 2003 Non-Final Office Action dated Feb. 13, 2006.
U.S. Appl. No. 10/374,000, filed Feb. 25, 2003 Non-Final Office Action dated May 20, 2009.
U.S. Appl. No. 10/374,000, filed Feb. 25, 2003 Non-final Office Action mailed Mar. 20, 2008.
U.S. Appl. No. 10/374,000, filed Feb. 25, 2003 Office Action dated Feb. 28, 2007.
U.S. Appl. No. 10/374,000, filed Feb. 25, 2003 Office Action dated Jul. 28, 2006.
U.S. Appl. No. 10/374,000, filed Feb. 25, 2003 Office Action mailed Sep. 30, 2008.
U.S. Appl. No. 10/374,000, filed Feb. 25, 2003 Response to Non-Final Office Action dated May 12, 2006.
U.S. Appl. No. 10/374,000, filed Feb. 25, 2003 Response to Office Action dated Dec. 28, 2006.
U.S. Appl. No. 10/374,000, filed Feb. 25, 2003 Response to Office Action dated Jun. 20, 2008.
U.S. Appl. No. 10/374,000, filed Feb. 25, 2003 Response to Office Action dated Mar. 30, 2009.
U.S. Appl. No. 10/374,000, filed Feb. 25, 2003 Response to Office Action dated May 28, 2007.
U.S. Appl. No. 10/374,000, filed Feb. 25, 2003 Response to Office Action dated Nov. 28, 2006.
U.S. Appl. No. 10/374,000, filed Feb. 25, 2003 Response to Office Action dated Oct. 31, 2007.
U.S. Appl. No. 10/374,000, filed Feb. 25, 2003 Response to Office Action dated Sep. 21, 2009.
U.S. Appl. No. 11/320,223, filed Dec. 28, 2005 Advisory Action dated Dec. 1, 2011.
U.S. Appl. No. 11/320,223, filed Dec. 28, 2005 Notice of Allowance dated Jan. 6, 2012.
U.S. Appl. No. 11/320,223, filed Dec. 28, 2005 Final Office Action dated Aug. 3, 2011.
U.S. Appl. No. 11/320,223, filed Dec. 28, 2005 Final Office Action dated Jun. 19, 2009.
U.S. Appl. No. 11/320,223, filed Dec. 28, 2005 Final Office Action dated Jun. 22, 2010.
U.S. Appl. No. 11/320,223, filed Dec. 28, 2005 Non-Final Office Action dated Feb. 13, 2008.
U.S. Appl. No. 11/320,223, filed Dec. 28, 2005 Non-Final Office Action dated Jan. 21, 2010.
U.S. Appl. No. 11/320,223, filed Dec. 28, 2005 Non-Final Office Action dated Mar. 16, 2011.
U.S. Appl. No. 11/320,223, filed Dec. 28, 2005 Non-Final Office Action dated Sep. 18, 2008.

(56) References Cited

OTHER PUBLICATIONS

U.S. Appl. No. 11/368,954, filed Mar. 6, 2006 Non-Final Office Action dated Jul. 21, 2009.
U.S. Appl. No. 11/368,954, filed Mar. 6, 2006 Notice of Allowance dated Jun. 24, 2010.
U.S. Appl. No. 11/368,954, filed Mar. 6, 2006 Final Office Action dated Jan. 27, 2010.
U.S. Appl. No. 11/368,954, filed Mar. 6, 2006 Preliminary Amendment dated Dec. 19, 2007.
U.S. Appl. No. 11/368,954, filed Mar. 6, 2006 Supplemental Non-final Office Action mailed Oct. 2, 2009.
U.S. Appl. No. 11/380,124, filed Apr. 25, 2006 Final Office Action dated Aug. 13, 2010.
U.S. Appl. No. 11/380,124, filed Apr. 25, 2006 Final Office Action dated Sep. 21, 2009.
U.S. Appl. No. 11/380,124, filed Apr. 25, 2006 Non-Final Office Action dated Apr. 26, 2010.
U.S. Appl. No. 11/380,124, filed Apr. 25, 2006 Non-Final Office Action dated Apr. 7, 2011.
U.S. Appl. No. 11/380,124, filed Apr. 25, 2006 Non-Final Office Action dated Jan. 16, 2009.
U.S. Appl. No. 11/380,124, filed Apr. 25, 2006 Non-Final Office Action dated Oct. 28, 2010.
U.S. Appl. No. 11/380,621, filed Apr. 27, 2006 Final Office Action dated Jan. 14, 2010.
U.S. Appl. No. 11/380,621, filed Apr. 27, 2006 Final Office Action dated Jan. 23, 2009.
U.S. Appl. No. 11/380,621, filed Apr. 27, 2006 Final Office Action dated Mar. 8, 2011.
U.S. Appl. No. 11/380,621, filed Apr. 27, 2006 Non-Final Office Action dated Jul. 1, 2009.
Navilyst Medical, Implantable Ports with PASV® Valve Technology, Product Overview,>>http://www.navilystmedical.com/Products/index.cfm/9>> last accessed Jun. 4, 2012.
Nucleus Cochlear Implant Systems; User Manual for the ESPrit 3G speech processor and accessories, Issue 2, Dec. 2001 http://www.cochlearamericas.com/PDFs/UserManualSprint.pdf.
Oct. 22, 2009 Declaration of Kelly Christian, Director of Product Development at BARD Access Systems, Inc, in support of and depicting a product on the market by Quinton Company approximately ten years prior to Oct. 22, 2009, 1 page.
PCT/US1999/028695 filed Dec. 3, 1999 International Preliminary Examination Report dated Apr. 21, 2001.
PCT/US1999/028695 filed Dec. 3, 1999 Search Report dated Apr. 11, 2000.
PCT/US2006/008022 filed Mar. 6, 2006 International Preliminary Report on Patentability dated Sep. 12, 2007.
PCT/US2006/008022 filed Mar. 6, 2006 Search Report dated Jul. 5, 2006.
PCT/US2006/008022 filed Mar. 6, 2006 Written Opinion dated Apr. 9, 2007.
PCT/US2006/015695 filed Apr. 25, 2006 Partial Search Report dated Sep. 29, 2006.
PCT/US2006/015695 filed Apr. 25, 2006 Search Report dated Jan. 11, 2007.
PCT/US2006/015695 filed Apr. 25, 2006 Written Opinion dated Jan. 11, 2007.
PCT/US2006/016056 filed Apr. 27, 2006 International Preliminary Report on Patentability dated Oct. 30, 2007.
PCT/US2006/016056 filed Apr. 27, 2006 Search Report dated Sep. 20, 2006.
PCT/US2006/016056 filed Apr. 27, 2006 Written Opinion dated Oct. 27, 2007.
PCT/US2006/049007 filed Dec. 21, 2006 International Preliminary Report on Patentability dated Jul. 1, 2008.
PCT/US2006/049007 filed Dec. 21, 2006 Search Report dated Oct. 1, 2007.
PCT/US2006/049007 filed Dec. 21, 2006 Written Opinion dated Oct. 1, 2007.
PCT/US2007/006776 filed Mar. 19, 2007 International Preliminary Report on Patentability dated Jan. 2, 2009.
PCT/US2007/006776 filed Mar. 19, 2007 Search Report, dated Dec. 18, 2007.
PCT/US2007/006776 filed Mar. 19, 2007 Written opinion, dated Dec. 18, 2007.
PCT/US2007/011015 dated May 7, 2007 Written Opinion dated Jun. 10, 2008.
PCT/US2007/011015 filed May 7, 2007 International Preliminary Report on Patentability dated Oct. 29, 2008.
PCT/US2007/011015 filed May 7, 2007 Search Report dated Jun. 10, 2008.
PCT/US2007/011456 filed May 11, 2007 Search Report dated Aug. 28, 2008.
PCT/US2007/011456 filed May 11, 2007 Written Opinion dated Aug. 28, 2008.
PCT/US2008/010520 dated Sep. 8, 2008 Search Report dated Feb. 24, 2009.
PCT/US2008/010520 filed Sep. 8, 2008 Written Opinion dated Feb. 24, 2009.
PCT/US2008/067679 filed Jun. 20, 2008 Search Report dated Sep. 30, 2008.
PCT/US2008/067679 filed Jun. 20, 2008 Written Opinion mailed on Sep. 30, 2008.
PCT/US2008/070330 filed Jul. 17, 2008 Search Report dated Dec. 1, 2008.
PCT/US2008/070330 filed Jul. 17, 2008 Written Opinion dated Dec. 1, 2008.
PCT/US2008/070345 filed Jul. 17, 2008 Search Report mailed on Dec. 1, 2008.
PCT/US2008/070345 filed Jul. 17, 2008 Written Opinion dated Dec. 1, 2008.
PCT/US2008/078976 filed Apr. 2, 2009 Search Report and Written Opinion dated Apr. 3, 2009.
PCT/US2009/062854 filed Oct. 30, 2009 International Preliminary Report on Patentability dated May 5, 2011.
PCT/US2009/062854 filed Oct. 30, 2009 International Search Report dated Dec. 10, 2009.
PCT/US2009/062854 filed Oct. 30, 2009 Written Opinion dated Dec. 10, 2009.
PCT/US2010/030256 filed Apr. 7, 2010 Search Report dated Jun. 4, 2010.
PCT/US2010/030256 filed Apr. 7, 2010 Written Opinion dated Jun. 4, 2010.
PCT/US2010/054994 filed Nov. 1, 2010 Search Report dated Jan. 10, 2011.
PCT/US2010/054994 filed Nov. 1, 2010 Written Opinion dated Jan. 10, 2011.
Port-A-Cath® P.A.S. Port® Systems by Deltec, Product Specifications, 1999.
Port-A-Cath® & Port-A-Cath® II Dual-lumen Implantable Venous Access Systems Product Specifications, 2005.
Port-A-Cath® and P.A.S. Port® Power P.A.C. Information Sheet, 2006.
Port-A-Cath® "Implantable Epidural, Aterial and Peritonial Access Systems" Internet Product Listing. <<http://web.archive.org/web/20001119035900/www.deltec.com/cPacspl.htm>> last accessed Jun. 4, 2012.
Port-A-Cath® "Many Port-A-Cath® System Choices" Product Brochure. 1996 SIMS Deltec, Inc.
Port-A-Cath® "Single-lumen Implantable Vascular Access Systems" Product Specifications. 2004 Smith Medical.
Rappolt, Richard T., et al. "Radiopaque Codification and X-ray Identification of Ingested Drugs." Ingestive Radiology, May-Jun. 1966.
Salis et al., "Maximal flow rates possible during power injection through currently available PICCs: An in-vitro study," J Vasc Interv Radiol 2004; 15:275-281.
Sandstede, Joern, "Pediatric CT," available online at www.multislice-ct.com, MultiSLICE-CT.com, version 02, May 2, 2003.
B. Braun, Easypump Product Page, accessed May 11, 2011.
B. Braun, Port Catheter Systems Product Page, accessed May 11, 2011.
JP 2008-509056 filed Apr. 25, 2006 Office Action dated Apr. 4, 2012.

(56) References Cited

OTHER PUBLICATIONS

PCT/US2009/035088 filed Feb. 25, 2009 International Search Report dated May 19, 2009.
PCT/US2009/035088 filed Feb. 25, 2009 Written Opinion dated May 19, 2009.
Smiths Medical, "Smiths Medical Launches Implantable Ports for Easy Viewing Under CT Scans" Press Release, Jan. 5, 2011.
U.S. Appl. No. 11/380,124, filed Apr. 25, 2006 Final Office Action dated Oct. 20, 2011.
U.S. Appl. No. 11/937,302, filed Nov. 8, 2007 Final Office Action dated Oct. 13, 2011.
U.S. Appl. No. 11/937,302, filed Nov. 8, 2007 Non-Final Office Action dated Jun. 18, 2012.
U.S. Appl. No. 12/267,160, filed Nov. 7, 2008 Final Office Action dated Jun. 1, 2012.
U.S. Appl. No. 12/267,160, filed Nov. 7, 2008 Non-Final Office Action dated Nov. 1, 2011.
U.S. Appl. No. 12/419,854, filed Apr. 7, 2009 Final Office Action dated Nov. 29, 2011.
U.S. Appl. No. 12/419,854, filed Apr. 7, 2009 Non-Final Office Action dated Jun. 26, 2012.
U.S. Appl. No. 12/617,981, filed Nov. 13, 2009 Non-Final Office Action dated Dec. 21, 2011.
U.S. Appl. No. 13/113,834, filed May 23, 2011 Non-Final Office Action dated Jul. 17, 2012.
U.S. Appl. No. 13/159,230, filed Jun. 13, 2011 Notice of Allowance dated Aug. 1, 2012.
U.S. Appl. No. 13/250,909, filed Sep. 30, 2011 Notice of Allowance dated Aug. 6, 2012.
BioEnterics Corporation, LAP-BAND® "Adjustable Gastric Banding System" Product Brochure Rev. G, Nov. 2000.
EP 06751411 filed Apr. 25, 2006 Decision Revoking the European Patent dated Aug. 1, 2012.
EP 10762377.9 filed Oct. 5, 2011 European Search Report dated Aug. 3, 2012.
Medtronic IsoMed® Constant-Flow Infusion System: Clinical Reference Guide for Hepatic Arterial Infusion Therapy, Revised Sep. 2000.
Nucleus Cochlear Implant Systems; User Manual for the ESPrit and ESPrit 22 speech processor and accessories, Issue 3, Apr. 2000.
Request for Inter partes Reexamination of U.S. Patent No. 7,785,302, filed Aug. 20, 2012.
Request for Inter partes Reexamination of U.S. Patent No. 7,947,022, filed Aug. 20, 2012.
Request for Inter partes Reexamination of U.S. Patent No. 7,959,615, filed Aug. 20, 2012.
U.S. Appl. No. 12/617,981, filed Nov. 13, 2009 Final Office Action dated Aug. 2, 2012.
U.S. Appl. No. 13/438,586, filed Apr. 3, 2012 Non-Final Office Action dated Sep. 19, 2012.
U.S. Appl. No. 29/382,235 filed Dec. 30, 2010 Non-Final Office Action dated Oct. 3, 2012.
U.S. Appl. No. 29/382,246 filed Dec. 30, 2010 Notice of Allowance dated Oct. 3, 2012.
CN 201080020088.3 filed Nov. 7, 2011 First Office Action dated Mar. 4, 2013.
ECRI Institute, Healthcare Product Comparison System, Dec. 2007.
EP 06751664.1 filed Apr. 27, 2006 First Examination Report dated Jul. 11, 2013.
EP 06845998.1 filed Dec. 21, 2006 Examination Report dated May 13, 2013.
EP 10183380.4 filed Apr. 25, 2006 European Search Report dated May 22, 2013.
EP 10183382.0 filed Apr. 25, 2006 European Search Report dated May 22, 2013.
EP 10183394.5 filed Apr. 25, 2006 European Search Report dated May 22, 2013.
EP 10183398.6 filed Apr. 25, 2006 European Search Report dated May 22, 2013.
EP 10762377.9 filed Oct. 5, 2011 Office Action dated Jul. 17, 2013.
EP 13158343.7 filed Mar. 8, 2013 Extended European Search Report dated May 14, 2013.
Ethanol Lock Technique for Prevention and Treatment of Central line-Associated Bloodstream Infections (Nebraska) Aug. 13, 2011, Accessed: Jun. 29, 2013 http://www.nebraskamed.com/app_files/pdf/careers/education-programs/asp/tnmc_etohlock_final.pdf.
JP 2012-156976 filed Jul. 12, 2012 Submission of Documents by Third Party dated May 14, 2013.
Medcomp Dialysis and Vascular Access Products (Medcomp) Jun. 30, 2009, Accessed Jun. 29, 2013 http://www.medcompnet.com/products/flipbook/pdf/PN2114G_Medcomp_Catalog.pdf.
PCT/US2013/031035 filed Mar. 13, 2013 International Search Report and Written Opinion dated Jun. 3, 2013.
Takeuchi, Syuhei et al., "Safety Considerations in the Power Injection of Contrast Medium via a Totally Implantable Central Venous Access System," Japan Journal of Interventional Radiology vol. 20, No. 1, pp. 27-30, Jan. 2005.
U.S. Appl. No. 11/380,124, filed Apr. 25, 2006 Notice of Allowance dated Apr. 29, 2013.
U.S. Appl. No. 12/419,854, filed Apr. 7, 2009 Advisory Action dated May 17, 2013.
U.S. Appl. No. 13/438,586, filed Apr. 3, 2012 Advisory Action dated May 29, 2013.
U.S. Appl. No. 13/438,586, filed Apr. 3, 2012 Final Office Action dated Mar. 7, 2013.
U.S. Appl. No. 13/471,219, filed May 14, 2012 Non-Final Office Action dated Jul. 10, 2013.
U.S. Appl. No. 13/571,088, filed Aug. 9, 2012 Final Office Action dated Jul. 16, 2013.
U.S. Appl. No. 13/776,451, filed Feb. 25, 2013 Non-Final Office Action dated Jul. 24, 2013.
U.S. Appl. No. 13/853,942, filed Mar. 29, 2013 Non-Final Office Action dated Jul. 26, 2013.
U.S. Appl. No. 95/002,089, filed Aug. 20, 2012 Action Closing Prosecution dated Jun. 12, 2013.
U.S. Appl. No. 95/002,090, filed Aug. 20, 2012 Action Closing Prosecution dated Jun. 12, 2013.
U.S. Appl. No. 95/002,092, filed Aug. 20, 2012 Action Closing Prosecution dated Jun. 12, 2013.
CN 200980153471.3 filed Jun. 30, 2011 Third Office Action dated May 28, 2014.
EP 10 831 973.2 filed May 30, 2012 Extended European Search Report dated Jul. 4, 2014.
EP 10183394.5 filed Apr. 25, 2006 Opposition by Smiths Medical ASD, Inc. dated Apr. 25, 2014.
JP 2012-156976 filed Jul. 12, 2012 Notice of Reasons for Refusal dated Apr. 8, 2014.
JP 2012-504826 filed Oct. 6, 2011 First Office Action dated Mar. 4, 2014.
U.S. Appl. No. 12/419,854, filed Apr. 7, 2009 Notice of Allowance dated Apr. 7, 2014.
U.S. Appl. No. 13/110,734, filed May 18, 2011 Non-Final Office Action dated Jul. 7, 2014.
U.S. Appl. No. 13/524,712, filed Jun. 15, 2012 Advisory Action dated May 7, 2014.
U.S. Appl. No. 13/524,712, filed Jun. 15, 2012 Final Office Action dated Mar. 3, 2014.
U.S. Appl. No. 13/776,517, filed Feb. 25, 2013 Final Office Action dated Jun. 30, 2014.
U.S. Appl. No. 13/776,517, filed Feb. 25, 2013 Non-Final Office Action dated Feb. 27, 2014.
Bard Access Systems, BardPort and X-Port Implanted Ports Brochure, © 2007.
Bard Access Systems, BardPort, Slim Port and X-Port Instructions for Use, May 2003.
Bard Access Systems, BardPort™ Implanted Ports Patient Information, Feb. 1993.
Bard Access Systems, Ports Brochure, © 2003.
Bard Access Systems, Titanium Dome Implantable Port, http://www.bardacess.com, last accessed Jan. 10, 2012.
CN 200980153471.3 filed Jun. 30, 2011 First Office Action dated Dec. 25, 2012.

(56) References Cited

OTHER PUBLICATIONS

EP 06845998.1 filed Dec. 21, 2006 Examination Report dated Nov. 7, 2012.
JP 2007-558331 filed Mar. 6, 2006 Office Action dated Jan. 22, 2013.
PCT/US11/37038 filed May 18, 2011 Written Opinion and Search Report dated Aug. 30, 2011.
PCT/US2011/037038 filed May 18, 2011 International Preliminary Report on Patentability dated Nov. 29, 2012.
PCT/US2011/037038 filed May 18, 2011 International Search Report and Written Opinion dated Aug. 30, 2011.
U.S. Appl. No. 11/937,302, filed Nov. 8, 2007 Final Office Action dated Nov. 8, 2012.
U.S. Appl. No. 12/267,160, filed Nov. 7, 2008 Examiner's Answer dated Dec. 5, 2012.
U.S. Appl. No. 12/419,854, filed Apr. 7, 2009 Final Office Action dated Feb. 14, 2013.
U.S. Appl. No. 12/420,007, filed Apr. 7, 2009 Final Office Action dated Mar. 22, 2013.
U.S. Appl. No. 12/420,007, filed Apr. 7, 2009 Non-Final Office Action dated Oct. 16, 2012.
U.S. Appl. No. 13/113,834, filed May 23, 2011 Final Office Action dated Nov. 23, 2012.
U.S. Appl. No. 13/571,088, filed Aug. 9, 2012 Non-Final Office Action dated Feb. 27, 2013.
U.S. Appl. No. 95/002,089, filed Aug. 20, 2012 Office Action in and Order Granting/Denying Request for Inter Partes Reexamination dated Nov. 7, 2012.
U.S. Appl. No. 95/002,090, filed Aug. 20, 2012 Office Action in and Order Granting/Denying Request for Inter Partes Reexamination dated Nov. 7, 2012.
U.S. Appl. No. 95/002,092, filed Aug. 20, 2012 Office Action in and Order Granting/Denying Request for Inter Partes Reexamination dated Nov. 13, 2012.
CN 200980153471.3 filed Jun. 30, 2011 Second Office Action dated Sep. 18, 2013.
CN 201080020088.3 filed Nov. 7, 2011 Second Office Action dated Nov. 21, 2013.
CN 201080051911.7 filed May 16, 2012 First Office Action dated Dec. 27, 2013.
EP 06751411 filed Apr. 25, 2006 Decision of the Technical Board of Appeal dated Jul. 24, 2013.
EP 06845998.1 filed Dec. 21, 2006 Examination Report dated Feb. 6, 2014.
EP 10183382.0 filed Apr. 25, 2006 Intent to Grant dated Mar. 7, 2014.
EP 11784194.0 filed Nov. 29, 2012 extended European search report dated Feb. 21, 2014.
EP 13158343.7 filed Mar. 8, 2013 Examination Report dated Feb. 4, 2014.
JP 2007-558331 filed Mar. 6, 2006 Office Action dated Aug. 20, 2013.
JP 2012-156976 filed Jul. 12, 2012 Notice of Reasons for Refusal dated Aug. 27, 2013.
MX/a/2011/004499 filed Apr. 28, 2011 First Office Action dated Jul. 25, 2013.
PCT/US2013/056019 filed Aug. 21, 2013 International Search Report and Written Opinion dated Feb. 28, 2014.
U.S. Appl. No. 13/438,586, filed Apr. 3, 2012 Notice of Allowance dated Sep. 16, 2013.
U.S. Appl. No. 13/524,712, filed Jun. 15, 2012 Non-Final Office Action dated Oct. 22, 2013.
U.S. Appl. No. 13/776,517, filed Feb. 25, 2013 Non-Final Office Action dated Nov. 15, 2013.
U.S. Appl. No. 13/853,956, filed Mar. 29, 2013 Non-Final Office Action dated Dec. 3, 2013.
U.S. Appl. No. 13/853,961, filed Mar. 29, 2013 Non-Final Office Action dated Dec. 3, 2013.
CN 201080051911.7 filed May 16, 2012 Second Office Action dated Jul. 16, 2014.
EP 06845998.1 filed Dec. 21, 2006 Summons for Oral Proceedings dated Sep. 30, 2014.
JP 2013-209156 filed Oct. 4, 2013 Non-Final Office Action dated Oct. 7, 2014.
MX/a/2011/004499 filed Apr. 28, 2011 Second Office Action dated May 25, 2014.
U.S. Appl. No. 13/524,712, filed Jun. 15, 2012 Non-Final Office Action dated Aug. 21, 2014.
U.S. Appl. No. 13/776,517, filed Feb. 25, 2013 Notice of Allowance dated Sep. 23, 2014.
U.S. Appl. No. 13/853,956, filed Mar. 29, 2013 Non-Final Office Action dated Sep. 15, 2014.
U.S. Appl. No. 13/853,961, filed Mar. 29, 2013 Non-Final Office Action dated Sep. 12, 2014.
Bard Access Systems, Bad Port, SlimPort, X-Port Instructions for Use, 24 pages, Oct. 2012.
Bard Access Systems, PowerPort and PowerLoc CT Guide, 11 pages, Dec. 2009.
Bard Access Systems, PowerPort and PowerLoc Product Brochure, 6 pages, © 2007.
Bard Access Systems, PowerPort CT Guide, 16 pages, Mar. 2007.
Bard Access Systems, PowerPort Guidelines for CT Technologists, 1 page, Feb. 2007.
Bard Access Systems, PowerPort Guidelines for CT Technologists, 1 page, Jul. 2006.
Bard Access Systems, PowerPort Guidelines for Nurses, 1 page, Feb. 2007.
Bard Access Systems, PowerPort Guidelines for Physicians, 1 page, Feb. 2007.
Bard Access Systems, PowerPort Prescription Pad, 1 page, © 2007.
Bard Access Systems, PowerPort™ Implantable Port Product Information, © 2007.
Bard Access Systems, When in Doubt, SCOUT!, 1 page, © 2007.
Biotronik, Stratos Cardiac Resynchronization Therapy Pacemakers Technical Manual, 179 pages, © 2008.
Boston Scientific, Xcela™ Power Injectable PICC Directions for Use, 12 pages, © 2007.
CN 200980153471.3 filed Jun. 30, 2011 Fourth Office Action dated Nov. 15, 2014.
EP 06751664.1 filed Apr. 27, 2006 Second Examination Report dated Dec. 17, 2014.
JP 2012-504826 filed Oct. 6, 2011 Second Office Action dated Nov. 17, 2014.
MX/a/2011/004499 filed Apr. 28, 2011 Third Office Action dated Jan. 21, 2015.
PFM Medical, Xcela™ Power Injectable Port Directions for Use, 15 pages, © 2008.
STD Manufacturing, Brochure with a Hickman port, 1 page, date unknown.
U.S. Appl. No. 13/524,712, filed Jun. 15, 2012 Notice of Allowance dated Dec. 12, 2014.
U.S. Appl. No. 13/571,088, filed Aug. 9, 2012 Non-Final Office Action dated Jan. 7, 2015.
B. Braun, Access Port Systems, Celsite® Product Information, 19 pages, Nov. 2005.
Bard Access Systems, Devices for Small Patients, © 2003.
Bard Access Systems, M.R.I. Dual Port with Septum-Finder Ridge IFU, 2 pages, © 1993.
Bard Access Systems, PowerPort Implanted Port with Open-Ended Catheter Instructions for Use, 8 pages, Dec. 2006.
Bard Access Systems, PowerPort Information for the Patient, 5 pages, © 2006.
Bard Access Systems, PowerPort Product Brochure, 8 pages, © 2009.
Department of Health and Human Services, PowerPort 510(k) FDA Clearance, Jan. 25, 2007.
EP 13158343.7 filed Mar. 8, 2013 Summons to Attend Oral Proceedings dated Oct. 20, 2014.

* cited by examiner

OVERMOLDED ACCESS PORT INCLUDING ANCHORING AND IDENTIFICATION FEATURES

CROSS-REFERENCE TO RELATED APPLICATIONS

This application claims the benefit of U.S. Provisional Patent Application No. 61/262,126, filed Nov. 17, 2009, and entitled "Implantable Overmolded Access Port Including Anchoring Identification Feature," which is incorporated herein by reference in its entirety.

BRIEF SUMMARY

Briefly summarized, embodiments of the present invention are directed to an access port for providing subcutaneous access to a patient. In particular, in one implementation the access port is implanted in the patient's body, then is fluidly connected to a catheter that has been introduced into the patient's vasculature. So positioned and configured, the access port can be transcutaneously accessed by a needle or other infusion/aspiration device so as to administer medicaments to the patient's vasculature via the port and catheter, or to aspirate blood or other fluids therefrom.

In one embodiment, the port includes an internal body defining a fluid cavity that is accessible via a septum. A compliant outer cover including silicone is disposed about at least a portion of the body. A flange is included with the port body and is covered by the outer cover. The flange radially extends about a perimeter of the port body proximate the septum so as to impede penetration of a needle a substantial distance into the outer cover, such as in instances where the needle misses the septum while attempting to access the port.

In one embodiment, the flange of the access port can further include both an anchoring feature for securing the outer cover to the port body and an identification feature observable via x-ray imaging technology for conveying information indicative of at least one attribute of the access port. The outer cover also provides a suitable surface for application of an antimicrobial/antithrombotic coating.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Figure 1A:
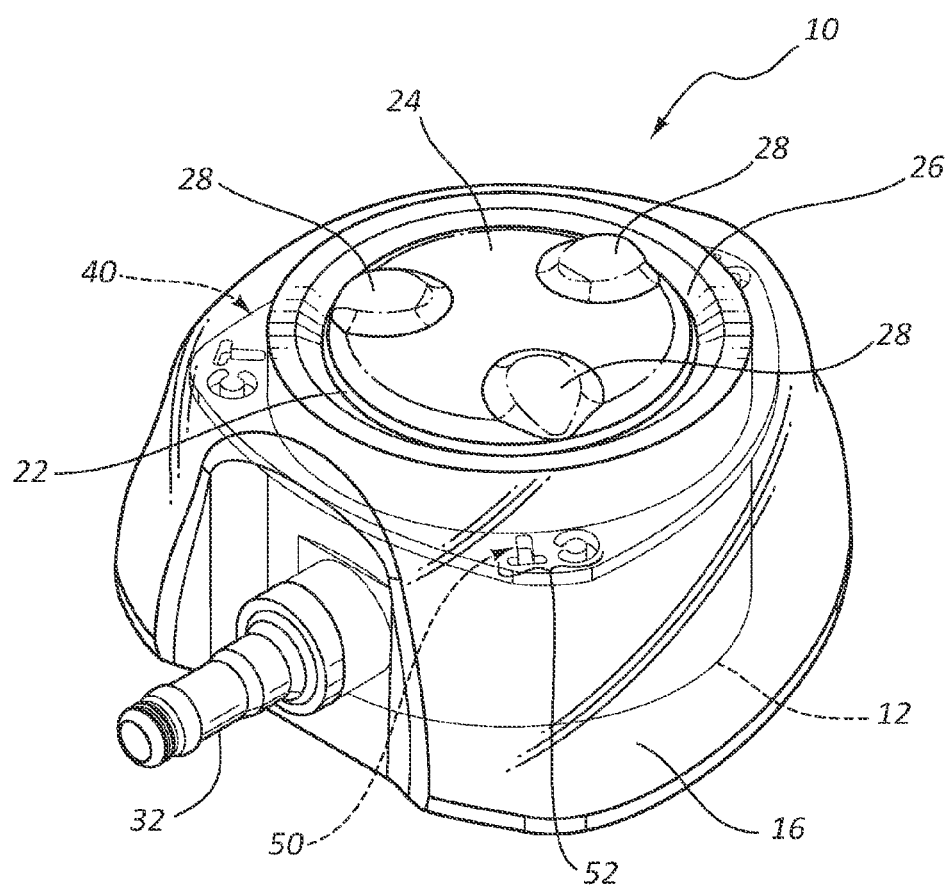
FIGS. 1A-1D are various views of an implantable overmolded access port according to one embodiment.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

FIGS. 1A-14B depict various features of embodiments of the present invention, which are generally directed to an access port for providing subcutaneous access to the body of a patient. In particular, in one implementation the access port is implanted in the patient's body, then is fluidly connected to a catheter that has been introduced into the patient's vasculature. So positioned and configured, the access port can be transcutaneously accessed by a needle or other infusion/aspiration device so as to administer medicaments to the patient's vasculature via the port and catheter, or to aspirate blood or other fluids therefrom.

Further, in embodiments to be described herein, the access port includes a compliant outer cover that increases patient comfort upon implantation and provides for enhanced options for suturing or otherwise securing the port within the patient's body. In addition, the compliant outer cover in one embodiment includes a biocompatible material such as silicone that provides a suitable surface on which an antimicrobial and/or antithrombotic coating can be applied in order to reduce patient risk or infection as a result of implantation of the access port. Additional features of the access port include, in one embodiment, identification features for identifying an attribute of the port via x-ray imaging, and anchoring features for securing the outer cover to the internal port body.

Reference is first made to FIGS. 1A-2D, which show various views of an implantable access port ("port"), generally designated at 10, according to one embodiment. As shown, the port 10 includes an internal body 12 that defines a bottom surface 14 and a fluid cavity 20 (FIG. 2A). An outer cover 16, to be discussed further below, is disposed about the body 12 to substantially cover it, with the exception of an opening 22 to the fluid cavity 20 and a penetrable septum 24 that is placed in the opening to cover the fluid cavity.

Figure 1B:
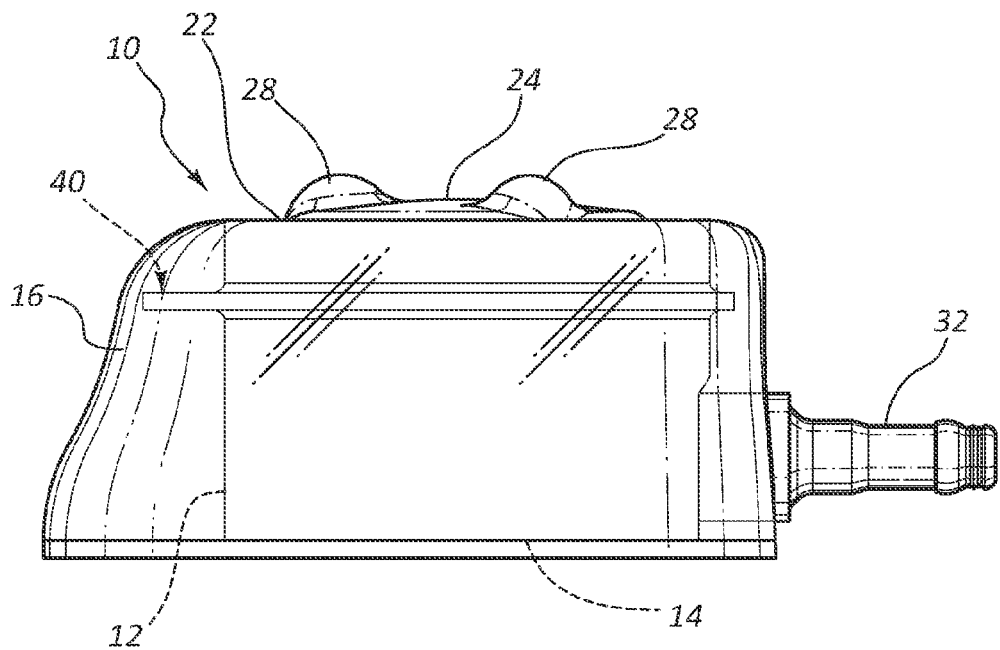
Figure 1C:
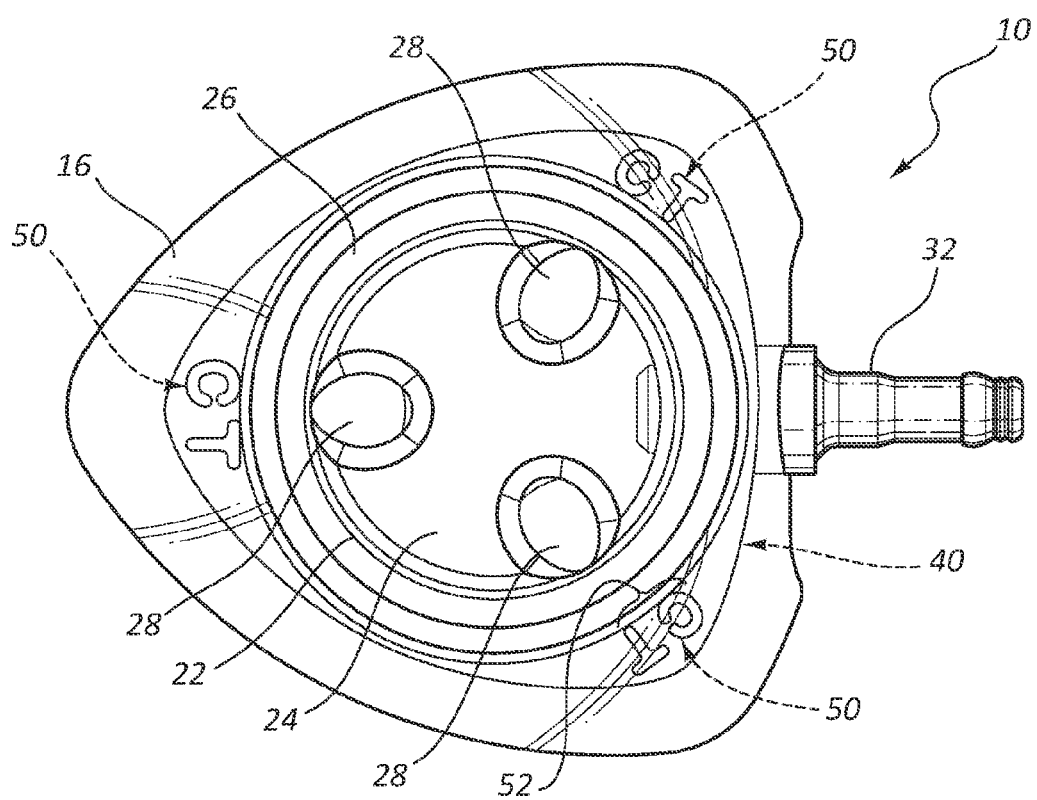

In greater detail, the septum 24 in the illustrated embodiment is held in place within the opening 22 of the fluid cavity 20 by a retaining ring 26 that is inserted into the opening 22 to engage the port body 12 in an interference fit. The outer cover 16 covers the surface of the body 12 of the port 10 up to a circular region about the retaining ring 26, as best seen in FIG. 1C. The outer cover can include other configurations in addition to what is explicitly shown in the accompanying figures.

In the present embodiment, the body 12 of the port 10 includes titanium or other suitable metallic material. In other embodiments to be described herein, the port body includes non-metallic materials. Additional details of the port 10 include a plurality of palpation features 28 included on a top surface of the septum 28 to assist in identification of the port after subcutaneous placement, and a fluid outlet 30 in fluid communication with the fluid cavity 20. A stem 32 defining a conduit is fixedly received within the fluid outlet 30 so as to provide a fluid pathway between the fluid cavity 20 and a catheter attached to the stem.

As mentioned, the outer cover 16 includes a compliant material and covers the port body 12. In one embodiment, the outer cover 16 includes silicone of 30 Shore A durometer, a biocompatible material, though it is appreciated that other suitable biocompatible and compliant materials can also be employed, including thermoplastic elastomers. Due to its compliant nature, the outer cover 16 provides increased comfort for the patient's body when implanted therein. Additionally, the outer cover 16 is pierceable by a needle to enable sutures to be secured through any number of locations in the outer cover to facilitate ease of securing the port within the patient's body.

Furthermore, the compliant outer cover 16 in one embodiment provides a suitable surface for the application of one or more coatings for the part 10. This is true in cases, for instance, where the port body 12 includes titanium or other metal, or an acetyl resin sold under the name DELRIN™, materials where coatings have been traditionally relatively difficult to adhere to.

In one example embodiment, an antimicrobial and/or antithrombotic coating(s) can be applied to the surface of the outer cover 16 in order to prevent the growth of microbes and/or formation of thrombus on or around the port 10. Non-limiting examples of coatings that may be applied to the outer cover 16 of the port 10 can be found in the following: U.S. Patent Application Publication No. 2007/0003603, filed Aug. 1, 2005, and entitled "Antimicrobial Silver Compositions;" U.S. Application Publication No. 2007/0207335, filed Feb. 8, 2007, and entitled "Methods and Compositions for Metal Nanoparticle Treated Surfaces;" and U.S. Application Publication No. 2007/0293800, filed Apr. 25, 2007, and entitled "Antimicrobial Site Dressings." Further coating examples can be found in the following: U.S. Pat. No. 6,808,738, entitled "Method of Making Anti-Microbial Polymeric Surfaces;" U.S. Pat. No. 6,475,516, entitled "Drug Delivery via Therapeutic Hydrogels;" and U.S. Patent Application No. 2004/0086568, filed Feb. 26, 2002, and entitled "Method of Making Anti-Microbial Polymeric Surfaces." Each of the afore-mentioned patents and applications is incorporated herein by reference in its entirety. Other coatings can also be employed as may be appreciated by one skilled in the art.

In one embodiment, an antimicrobial coating applied to the outer cover includes silver and further includes a component to prevent apparent discoloration of the outer cover, such as a dye component commonly known as Brilliant Green, CAS number 633-03-4. In yet another embodiment, an antimicrobial, antithrombotic, or other suitable material can be added to the outer cover materials and configured to elute therefrom at a desired rate in order to provide desired properties to the surface of the outer cover. The outer cover in one embodiment can be colored to fall within a specific color range on the PANTONE® Matching System (Pantone Inc., Carlstadt, N.J.), such as Pantone 3272M and proximate colors, for instance.

Note that the body 12 and the retaining ring 26 of the port 10 shown in the present embodiment of FIGS. 1A-2D include titanium. In some embodiments described below, other materials are employed for the port body. It should be remembered that, in addition to what is disclosed herein, other suitable materials can be employed for the various components of the port without departing from the spirit of the embodiments described herein.

In accordance with one embodiment, the port 10 further includes a flange 40 that extends radially about a perimeter of the body 12 of the port. As best seen in FIG. 1B, the flange 40 is positioned circumferentially about and proximate to the septum 24 and opening 22 of the fluid cavity 20. So configured, the flange 40 functions as a needle guard for preventing penetration by a needle or other infusion/aspiration device into a portion of the outer cover 16 relatively close to the septum 24 of the port 10. This in turn prevents a user of the needle from penetrating the compliant outer cover 16 and thus believing the needle has accessed the septum 24, which in one embodiment also includes a complaint material such as silicone. In such a case, needle penetration into the outer cover by the user will be impeded by the flange 40, which will indicate to the user the need to re-insert the needle to access the septum 24, thus preventing further problems. It is appreciated that in the present embodiment the flange is formed integrally with the port body and thus includes titanium. In other embodiments, however, the flange can be separately manufactured, can include other suitable materials, can extend from other areas of the port body other than proximate the septum, and can include different shapes and configurations.

In one embodiment, the flange 40 also serves to enable identification of the port as including a particular characteristic or attribute. For instance, the flange 40 can include one or more identification features that are observable via x-ray or other similar imaging technology so as to enable identification of a corresponding attribute of the port after implantation thereof into the body of the patient. One example of an attribute that can be indicated by the identification feature is the ability of the port to participate in the infusion of fluids therethrough at a relatively high flow rate, commonly referred to as power injection. Such power injectability is useful, for instance, when injecting contrast media through the port 10 in connection with computed tomography ("CT") imaging procedures on the patient's body. Power injection flow through the port in one example is performed at a rate of about zero to five milliliters per second, though this can vary according to a number of factors.

Figure 1D:
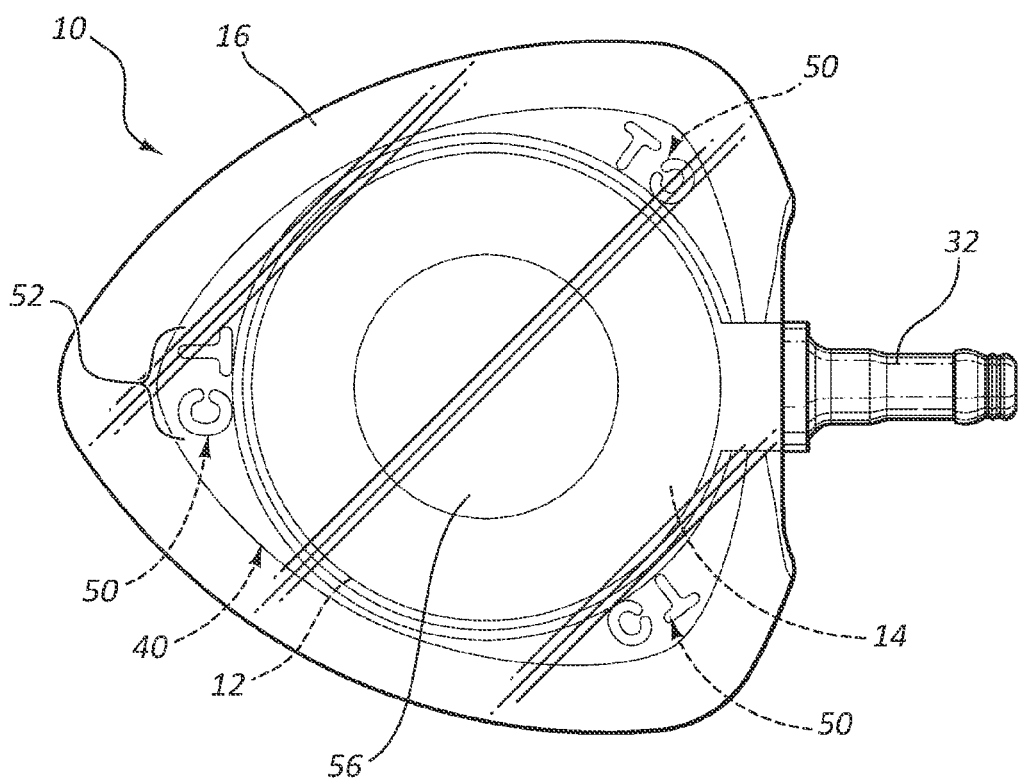
Figure 2A:
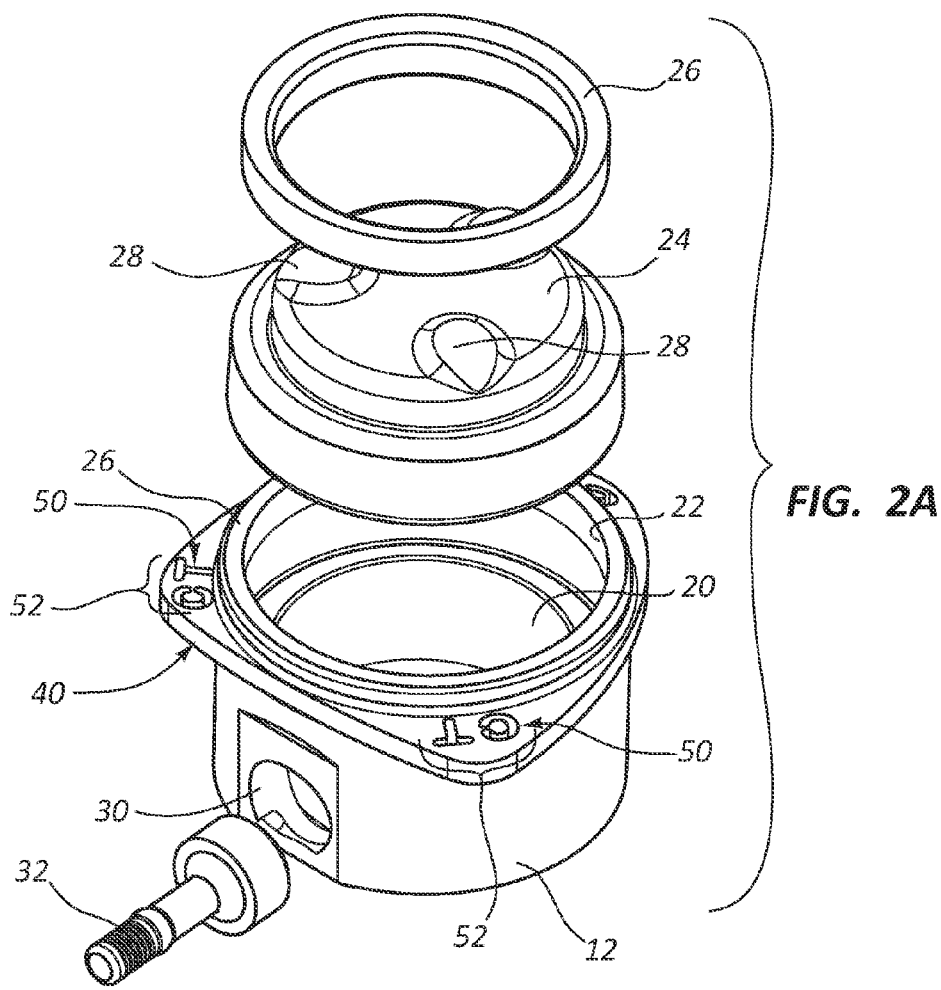
FIGS. 2A-2D are various views of the access port of FIGS. 1A-1D with the overmolding removed.
Figure 2B:
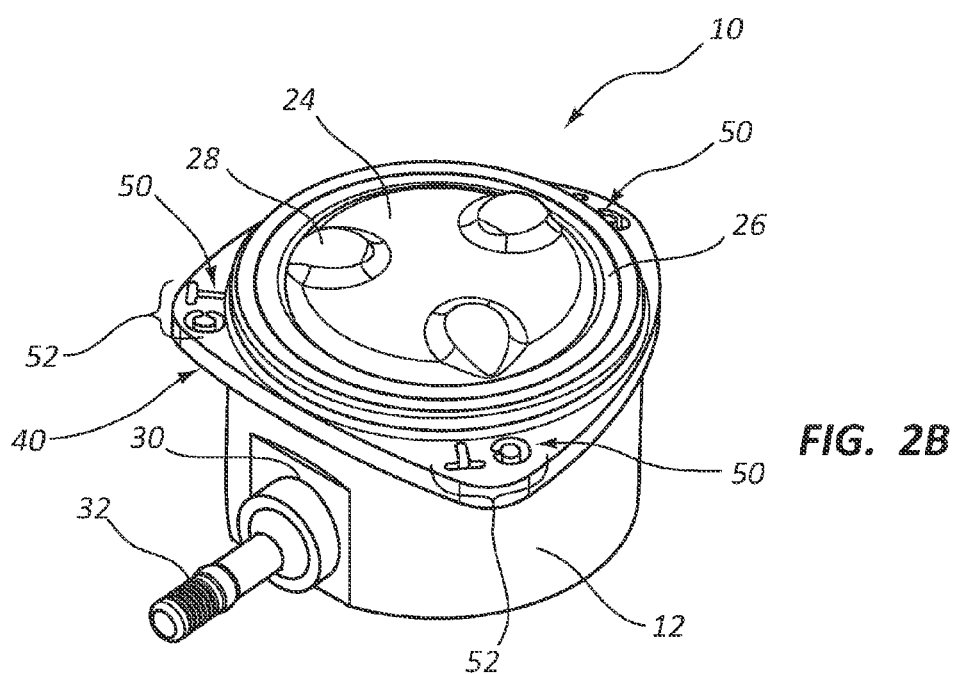
Figure 2C:
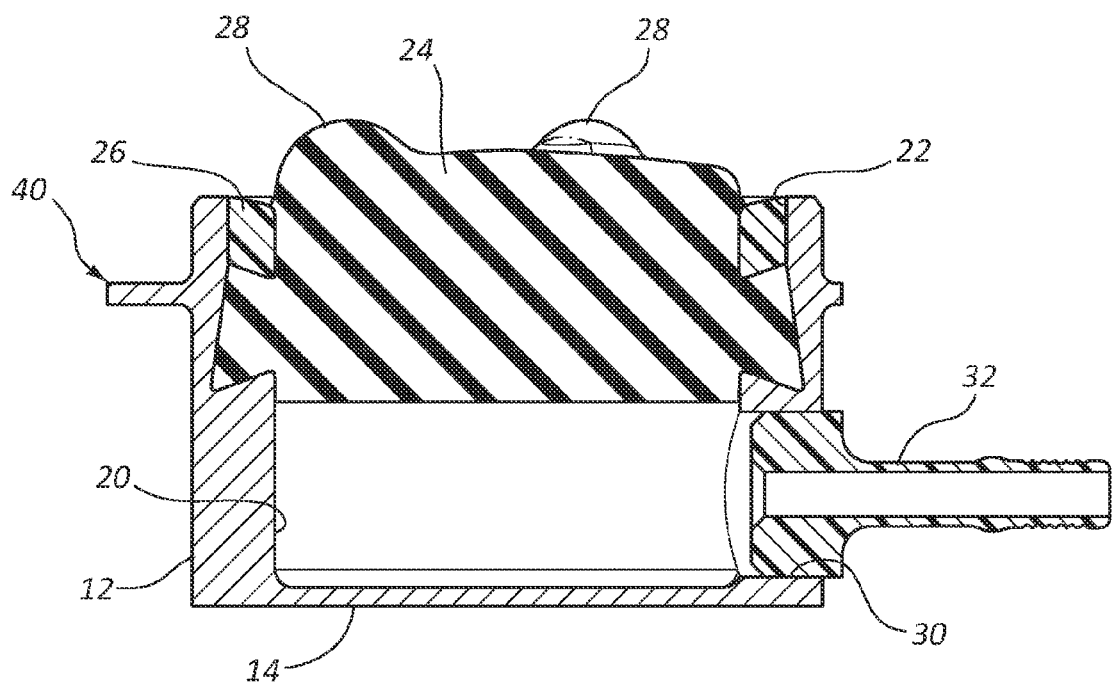
Figure 2D:
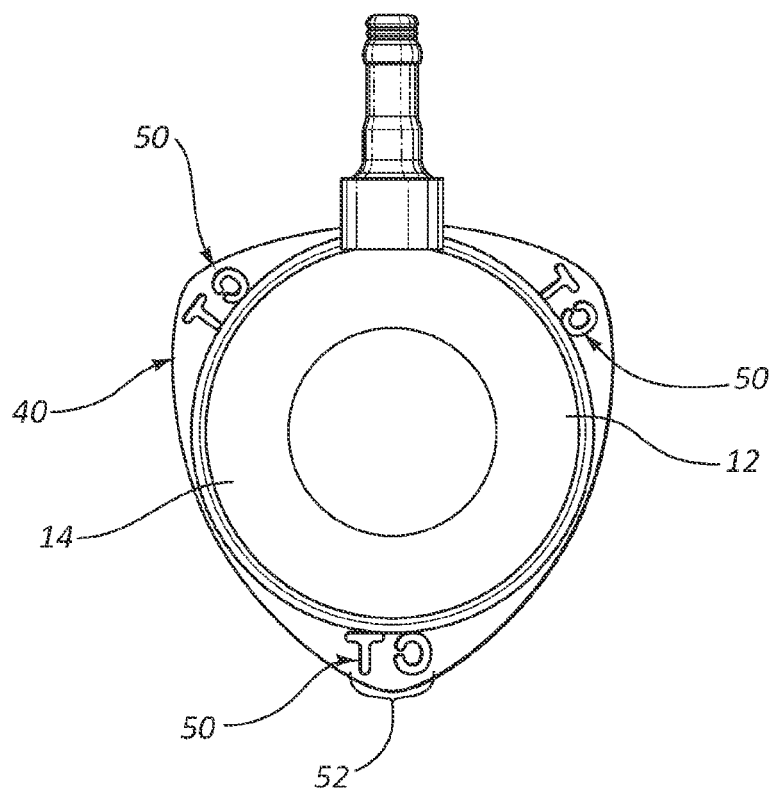

In accordance with the above, the port flange 40 in one embodiment includes one or more identification features 50, best seen in FIGS. 1C, 1D, and 2D. In particular, the identification features 50 of the present embodiment include alphanumeric indicia 52 that are defined in the body of the flange 40. In greater detail, the flange 40 in the present embodiment includes a set of three alphanumeric indicia 52, wherein each indicium includes the letters "CT" defined through the thickness of the flange so as to provide a radiographic contrast between the CT holes and the surrounding body of the flange when the port is imaged via x-ray. The orientation of the "CT" letters is such that observation thereof in an x-ray will indicate whether the port is properly positioned and oriented within the body of the patient.

It is contemplated that the identification features 50 described above can be one or more alphanumeric characters, such as the "CT" depicted in FIGS. 1A-2D. Additionally, the instant disclosure contemplates the use on the flange of other markings, such as one or more symbols, patterns, characters, designs, a combination thereof, etc. The identification feature(s) can be of any size, shape, or both in order to tailor the identification feature for the specific identification of one or more of a variety of attributes of the access port. Specifically, in one embodiment the identification feature(s) can convey information to a practitioner regarding the power-injectability of the implanted port, as has been discussed. Other examples of attributes the identification feature can convey include port type, catheter type, date of manufacture, lot number, part number, etc. In other embodiments, the identification feature can be defined in other ways.

In one embodiment, the flange 40 serves yet another function as an anchoring feature in securing engagement between the port body 12 and the outer cover 16. As mentioned above, the alphanumeric indicia ("CT") 52 in the present embodiment are defined as holes through the thickness of the flange 40, which flange is included with the internal body 12 of the port 10. During manufacture of the port 10, the outer cover 16 of the envelops the port body 12 via an overmolding process, wherein silicone or another suitable, flowable material is injected into a mold containing the port body 12 such that the silicone envelops the majority of the port body, including the flange 40. The silicone is then allowed to cure to form the outer cover 16. During the overmolding process, the flowable silicone flows through the holes of the CT indicia 52 and remains therein after curing is complete such that a bond in and through the CT holes is defined by the silicone, thus anchoring the outer cover 16 as a single piece to the port body 12 and preventing separation therebetween.

As will be seen further below, the anchoring features as described here can be modified from what is shown in FIGS. 1A-2D. In one embodiment, an adhesive can be used to adhere the outer cover 16 to the port body 12, especially about the circular termination of the outer cover proximate the port body opening 22. Adhering the outer cover in this area can serve to prevent seepage under the outer cover 16 of any coatings or layers applied to the external surface of the outer cover. Examples of suitable adhesives are available from NuSil Technology LLC of Carpinteria, Calif.

As best seen in FIG. 1D, in one embodiment, an insert 56 including the same material as the outer cover 16 is affixed to the bottom surface 14 of the internal port body 12 before overmolding of the outer cover occurs. The purpose of the insert 56 is to help stabilize and secure the internal port body 12 within the mold before the outer cover is overmolded on to the body. In one embodiment, both the outer cover 16 and the insert 56 include silicone such that both integrate together during the overmolding process. In another embodiment shown in FIG. 3F, a disk 70 including a suitable radiopaque material, such as titanium, can replace the insert 56 on the bottom surface 14 of the internal port body 12 and can include an identification feature 50 observable via interaction with x-ray imaging apparatus such that a characteristic or attribute of the port can be identified after implantation. In the illustrated embodiment, the disk includes alphanumeric cutouts of the letters "CT."

Figure 3A:
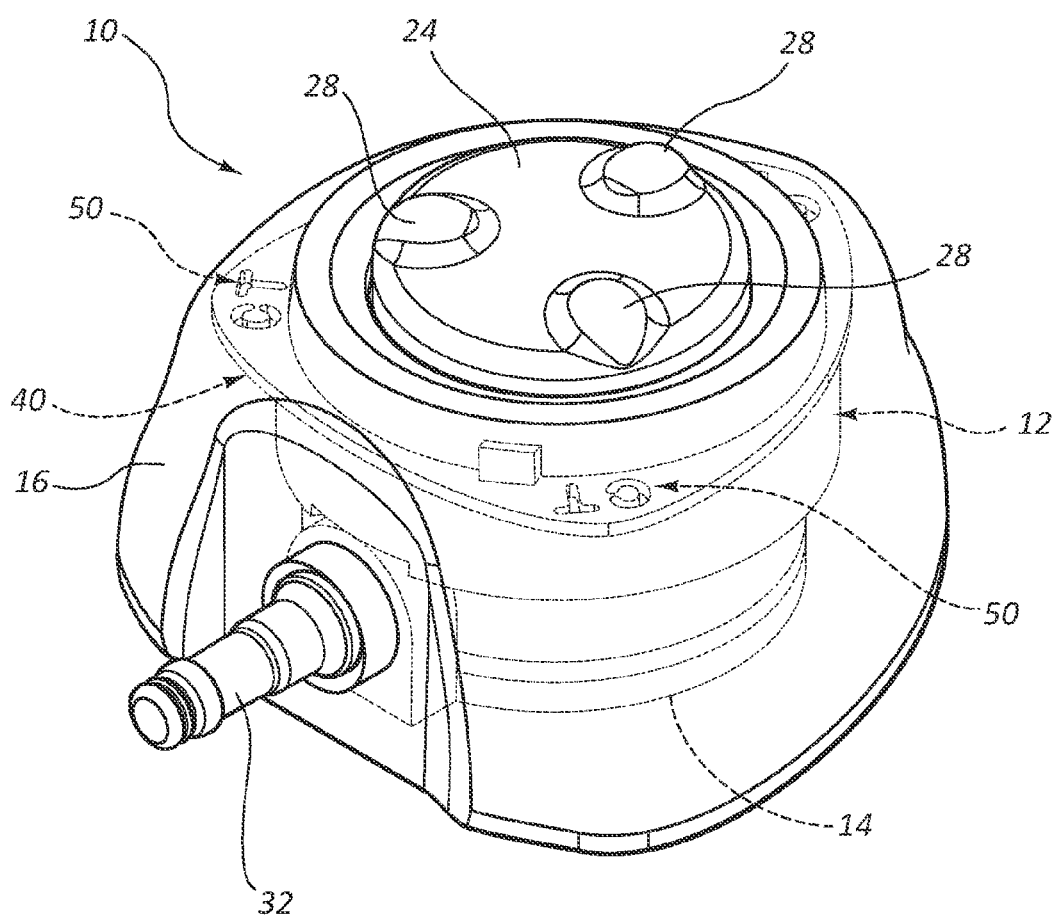
FIGS. 3A-3E are various views of an implantable overmolded access port according to one embodiment.
Figure 3B:
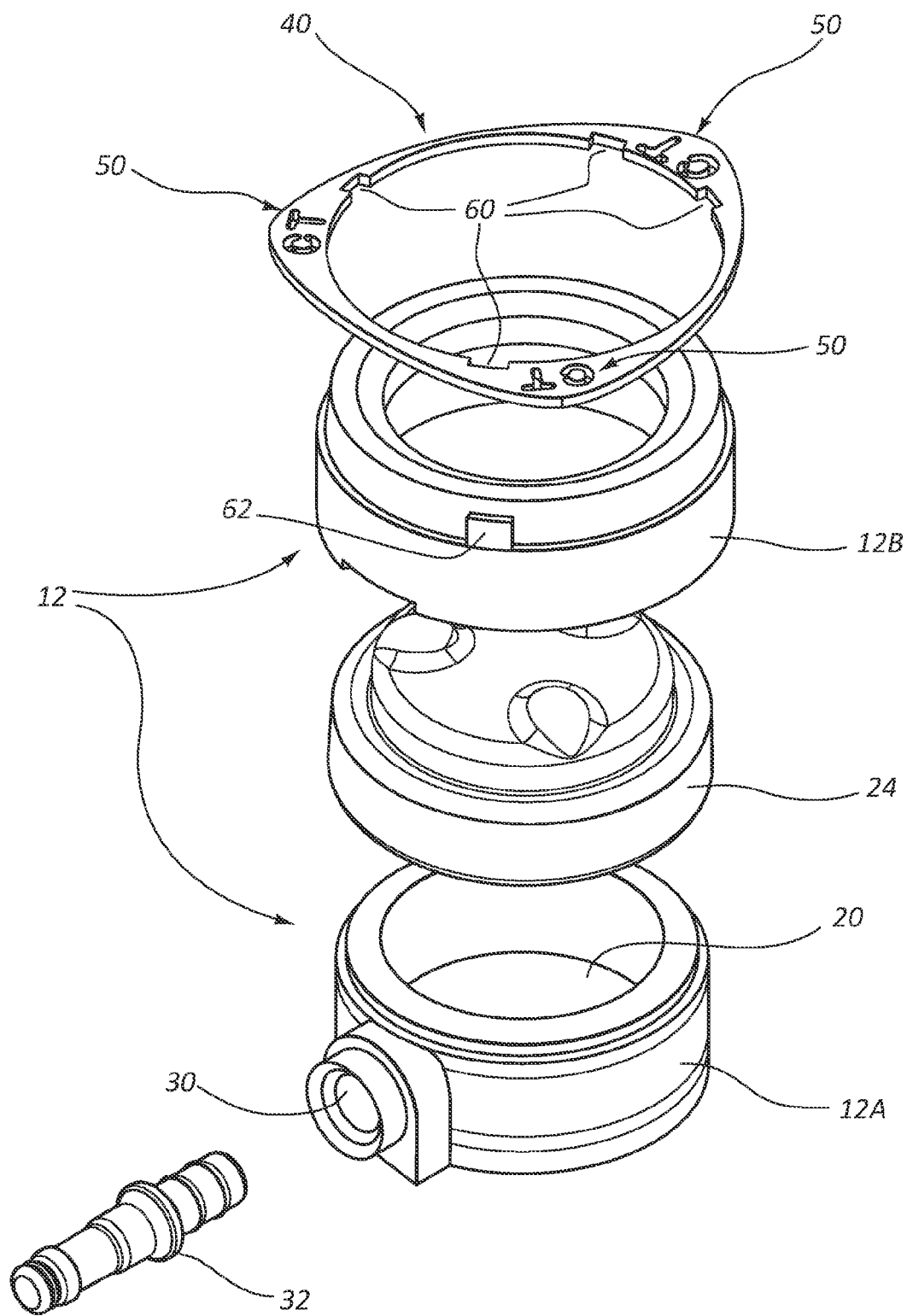

FIGS. 3A-3E depict various views of the port 10 according to another embodiment, wherein the internal body 12 of the port includes a thermoplastic, such as an acetyl resin commonly sold under the name DELRIN™. As best seen in FIG. 3B, the port body 12 includes a base 12A and a cap 12B that are mated together via ultrasonic welding or other suitable process to define the fluid cavity 20 and to capture therebetween the septum 24. As such, no retaining ring is employed as in the metallic port of the previous embodiment of FIGS. 1A-2D.

Figure 3C:
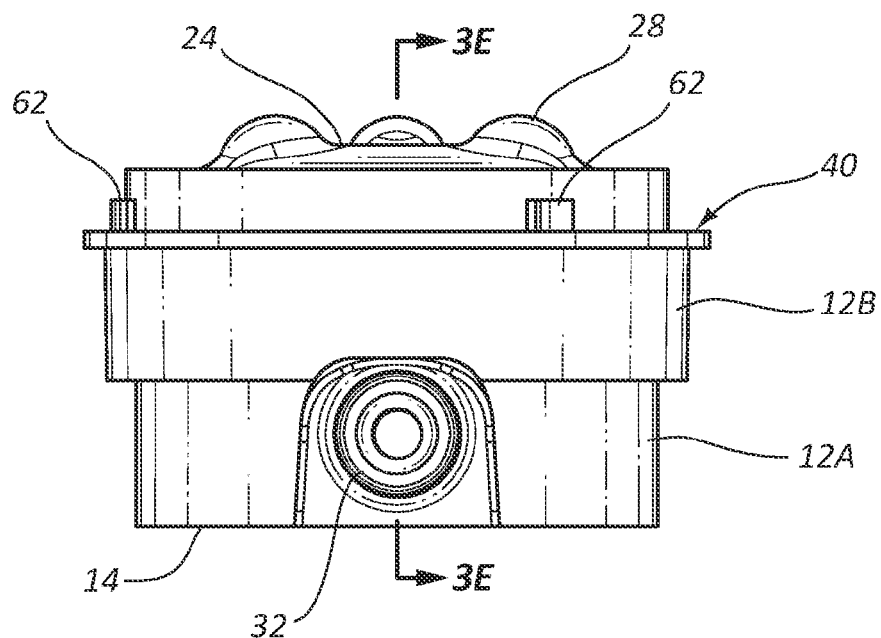
Figure 3D:
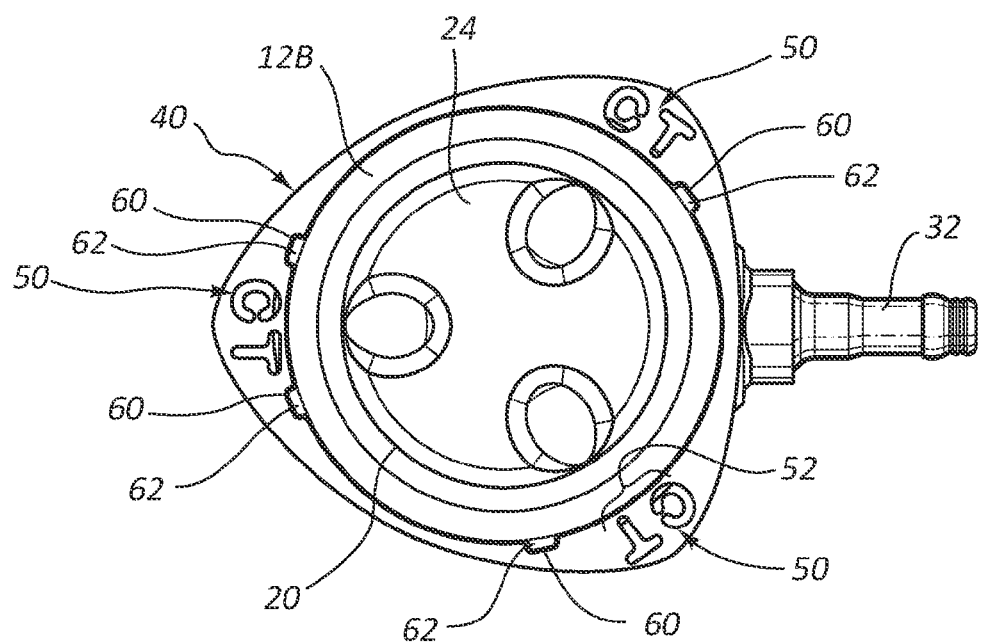
Figure 3E:
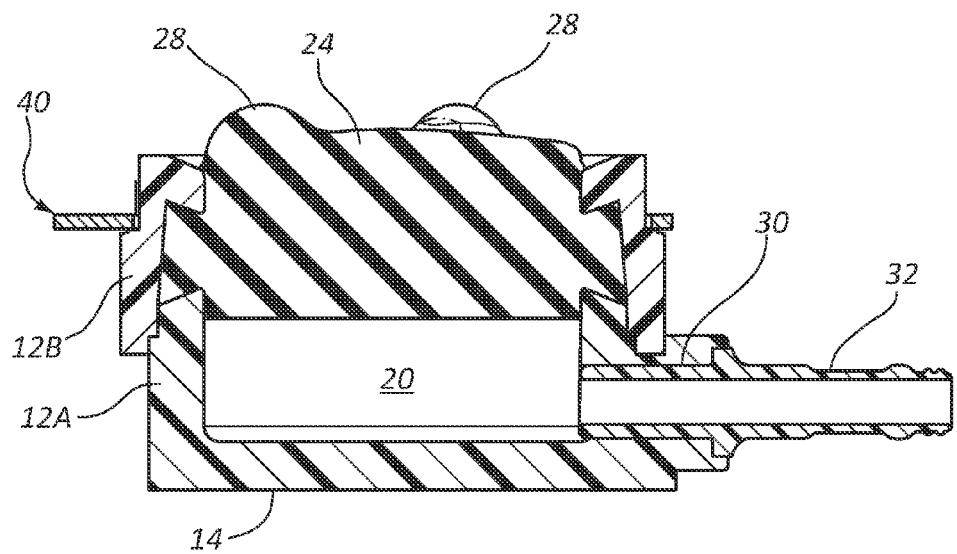
Figure 3F:
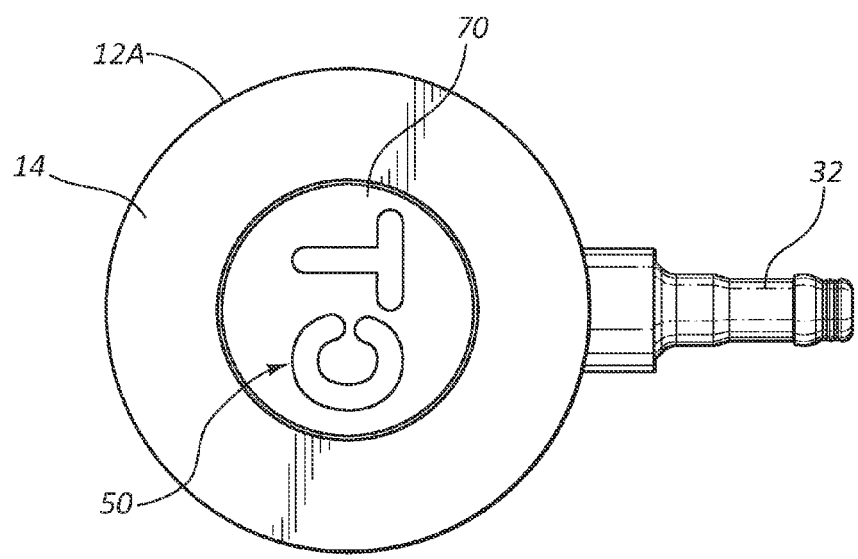
FIG. 3F is a bottom view of an access port body according to one embodiment.

The port 10 of FIGS. 3A-3E includes the flange 40 as a separately manufactured component that is attached to the body 12 of the port 10. Specifically, and with additional reference to FIG. 4, the flange 40 of the present embodiment includes a central hole 40A to enable the flange to receive the port body 12 therethrough and to sit atop a ledge defined on the cap 12B, as best seen in FIGS. 3B and 3C. A plurality of notches 60 are defined about the perimeter of the central hole 40A of the flange 40 and correspond with a plurality of extending tabs 62 included on the cap 12B on the ledge thereof. The notches 60 and corresponding tabs 62 are keyed relative to one another so as to enable the flange 40 to seat in only the correct orientation atop the ledge, that is, to ensure the alphanumeric indicia are positioned in the correct orientation with respect to the port.

In the present embodiment, after the flange 40 has been properly positioned on the cap 12B during manufacture as shown in FIG. 3C, the notches 60 thereof will be seated over the tabs 62 of the cap. The tabs 62 can then be deformed by a melting, mechanical, or other suitable deformation process so as to lock the flange 40 on the cap 12B and prevent its removal therefrom.

Figure 4:
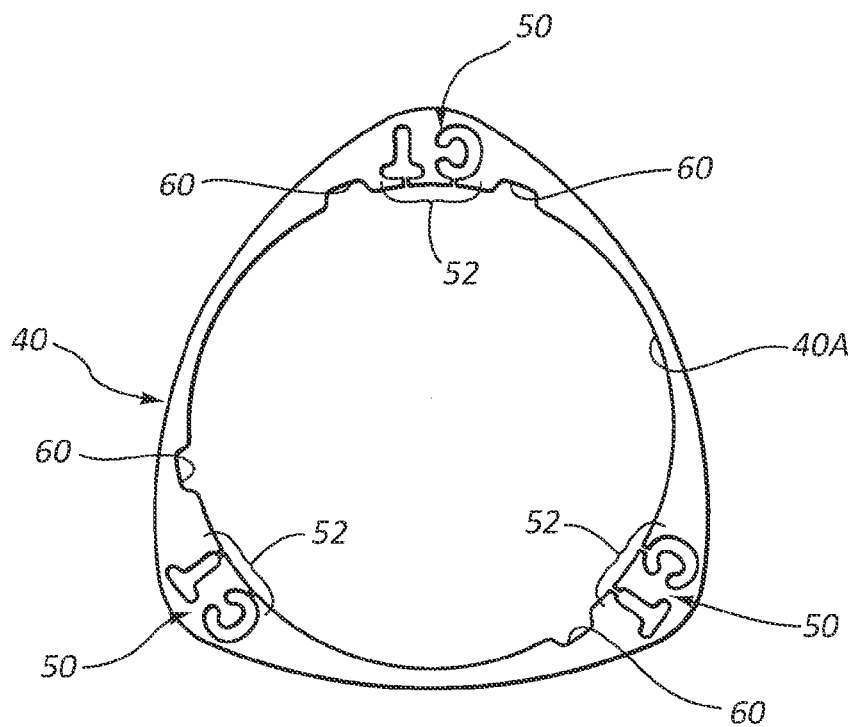
FIG. 4 is a top view of a port flange for use with the access port of FIGS. 3A-3E.

As mentioned, FIG. 4 shows further details of the flange 40, including the alphanumeric indicia 52 of each identification feature 50, the central hole 40A, and the notches 60. Note that in the present embodiment, the flange includes titanium and the outer perimeter of the flange 40 generally defines a bulged triangle with a corresponding one of the alphanumeric indicia 52, which indicia serve as both identification features and anchoring features for securing the outer cover 16 to the port body 12, positioned at each of the vertices of the triangle. The "CT" indicia 52 are formed in the flange 40 in one embodiment by wire EDM cutting, though other acceptable methods can also be employed including stamping, molding, etc. It is appreciated that the size, shape, and composition of the flange, together with the configuration of the identification features, can vary from what is shown and described herein. For instance, other suitable materials the flange may include can be found in U.S. Pat. No. 8,029,482, which is incorporated herein by reference in its entirety.

Figure 5:
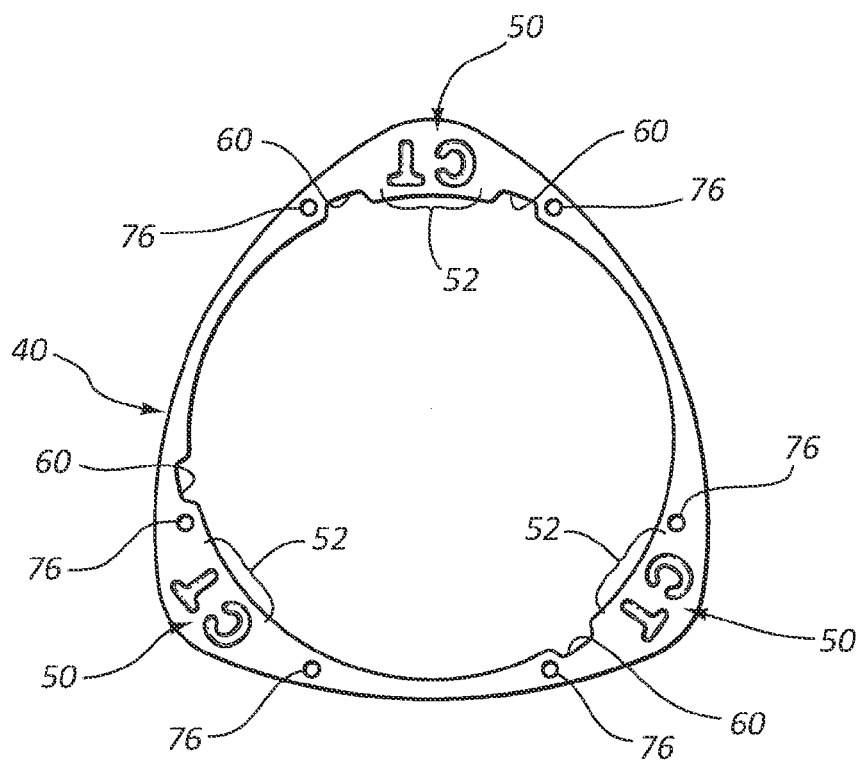
FIG. 5 is a top view of a port flange according to one embodiment.

FIGS. 5-9 show details of additional embodiments relating to the flange 40. FIG. 5 shows the flange 40 according to one embodiment, wherein the identification features 50—here represented as the alphanumeric indicia 52—are not defined through the entire thickness of the flange, but are only defined partially therethrough so as to form recessed features. In one embodiment, the indicia 52 are defined to a depth in the flange 40 of about 0.015 inch, the flange including a total thickness of about 0.020 inch, though other depths and flange thicknesses are possible. This enables the "CT" indicia 52 to be viewed visually (before implantation) only when the port 10 is viewed from a top-looking-down perspective, such as the perspective shown in FIGS. 1C and 3D. Further, the CT indicia 52 formed in this manner provide sufficient radiographic contrast to enable the indicia to be imaged via x-ray imaging after port implantation, thus serving the desired role as identification features for the port 10. The indicia 52 can be formed by wire EDM machining, laser etching, etc. In addition, a plurality of through holes 76 is defined through the thickness of the flange 40 to serve as anchoring features for the flange. The flange 40 is positioned similarly to that shown in FIGS. 1A-3E.

Note that in the above embodiment and in selected embodiments to follow, the identification features for identifying an attribute of the port are configured such that they are visually viewable (e.g., before implantation) from only predetermined perspectives, such as a top-looking-down perspective shown in FIG. 5 for instance. Such limited perspective visual viewing of the identification feature is useful in one embodiment to indicate to a clinician the top of the port; that is, when the port is placed top-side-up, the identification feature can be visually identified, indicating a proper orientation for inserting the port into the body of the patient. When the port is upside-down, however, the identification feature is not visually observable, thus indicating to the clinician that the port is upside-down. This feature can thus serve to eliminate confusion for the clinician as to the proper orientation of the port. In addition, it is appreciated that in one embodiment, all or a portion of the outer cover of the port can be made opaque so as to eliminate the possibility for a clinician to mistake the CT indicia cutouts of the flange for suture holes through which sutures are to pass.

Figure 6A:
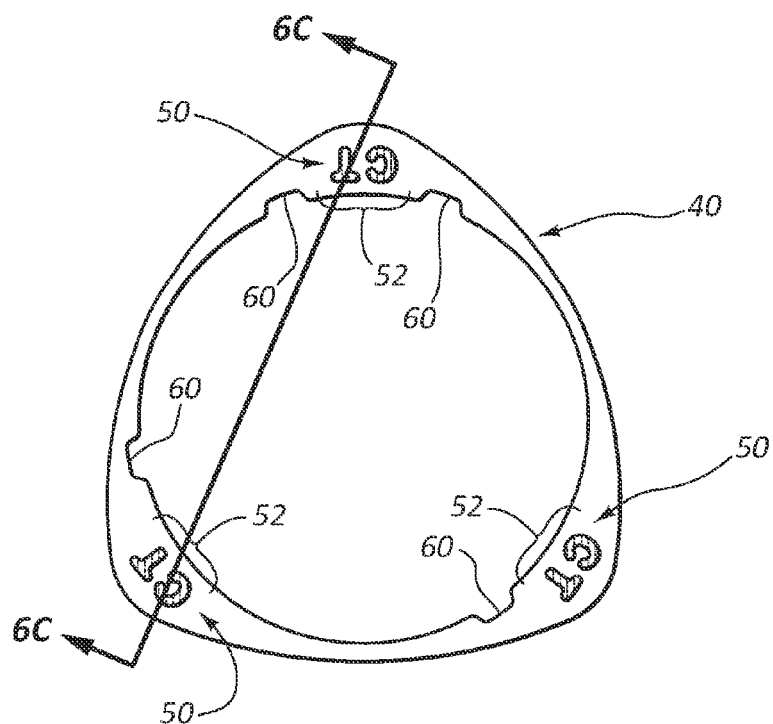
FIGS. 6A-6C are various views of a port flange and related components according to one embodiment.
Figure 6B:
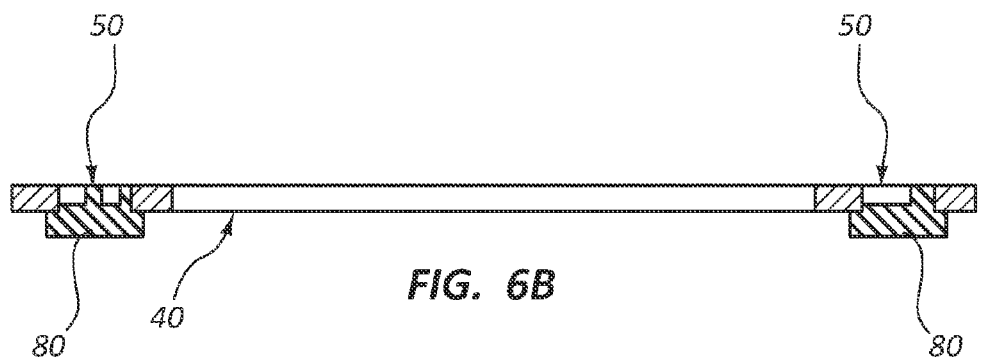
Figure 6C:
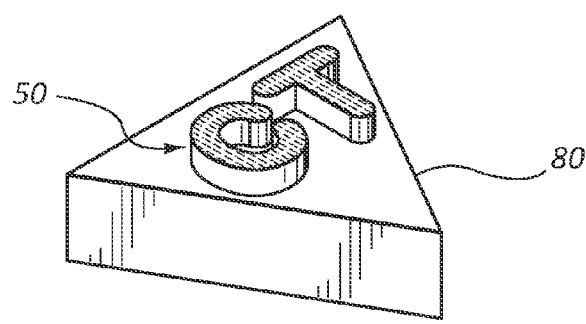

FIGS. 6A-6C show the flange 40 according to another embodiment, wherein the "CT" alphanumeric indicia 52, each serving as the identification feature 50, are defined as cutouts through the thickness of the flange, as in previous embodiments. A compliant, opaque triangular plug 80 defining the letters "CT" in raised relief to correspond with the "CT" of each of the indicia 52 is inserted into the "CT" cutout of each of the indicia so as to be retained thereby. So positioned, the plug enables the "CT" indicia 52 to be viewed visually (before implantation) only when the port 10 is viewed from a top-looking-down perspective, such as the perspective shown in FIGS. 1C and 3D. When visually viewed from the port bottom, the plug prevents the respective indicia 52 from being observed. Instead, the shape of the plug bottom, a triangle in the present embodiment, is seen. Note that the shape of the plug can vary, as can the raised relief on a top surface thereof in order to correspond with the cutout design of the indicia into which the plug is to be inserted.

Figure 7:
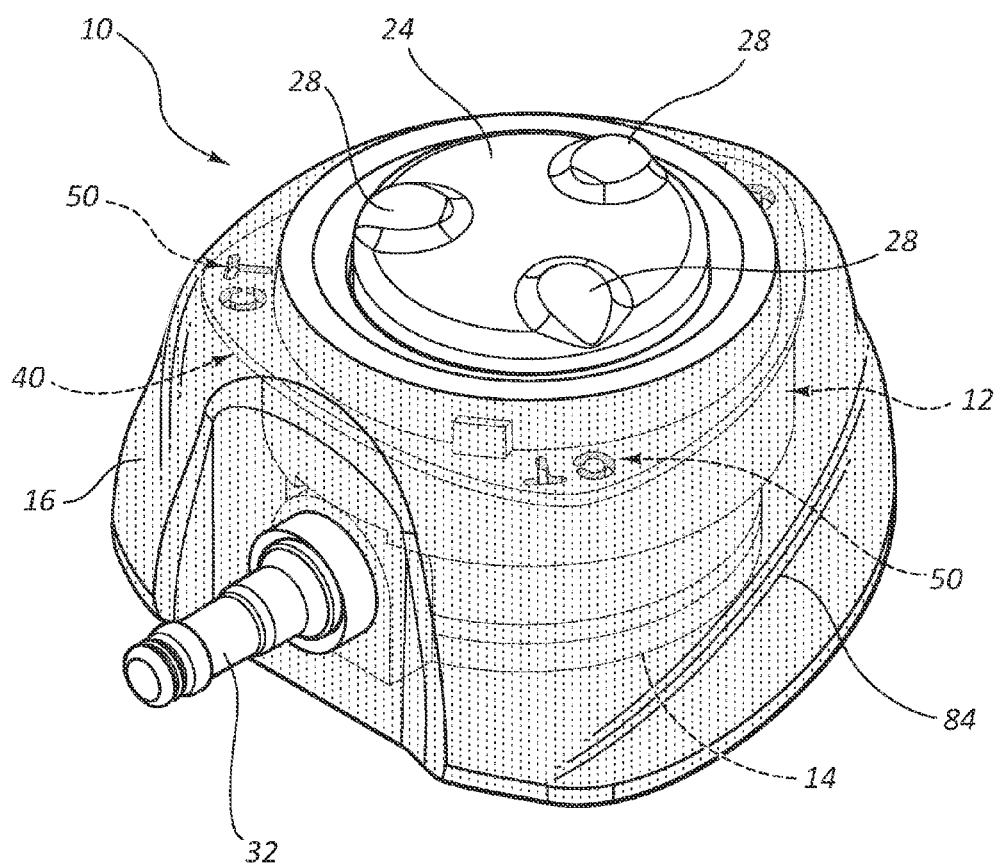
FIG. 7 is a perspective view of an implantable overmolded access port according to one embodiment.

FIG. 7 shows the port 10 according to one embodiment, wherein the outer cover 16 of the port includes a frosted surface 84 or otherwise obscured surface so as to render the outer cover opaque. The frosted surface 16 of the port 10 in one embodiment is achieved during the overmolding phase, wherein the surfaces of the mold used to overmold the outer cover 16 to the internal port body 12 include a roughened surface, achieved for instance via bead blasting of the mold surface. When the outer cover 16 is overmolded in such a mold, the frosted surface 84 of FIG. 7 results. It is appreciated that other suitable methods for providing a frosted or opaque surface to the outer cover 16 can also be employed. In yet another embodiment, only a bottom surface of the outer cover is frosted.

In another embodiment, a fabric or mesh structure can be incorporated/imbedded into the outer cover of the port so as to render it opaque. In yet another embodiment, instead of bead blasting, the mold surface can be treated to define thereon diamond-shaped mesh surface features that will impart to the port outer cover when molded therein a roughened, opaque surface. In yet another embodiment, logos or other features can be inscribed into the port outer cover, or included as surface features in the mold surface in which the outer cover is overmolded to the port body so as to render the outer cover at least partially opaque. These and other treatments for outer cover opacity are therefore contemplated.

Figure 8:
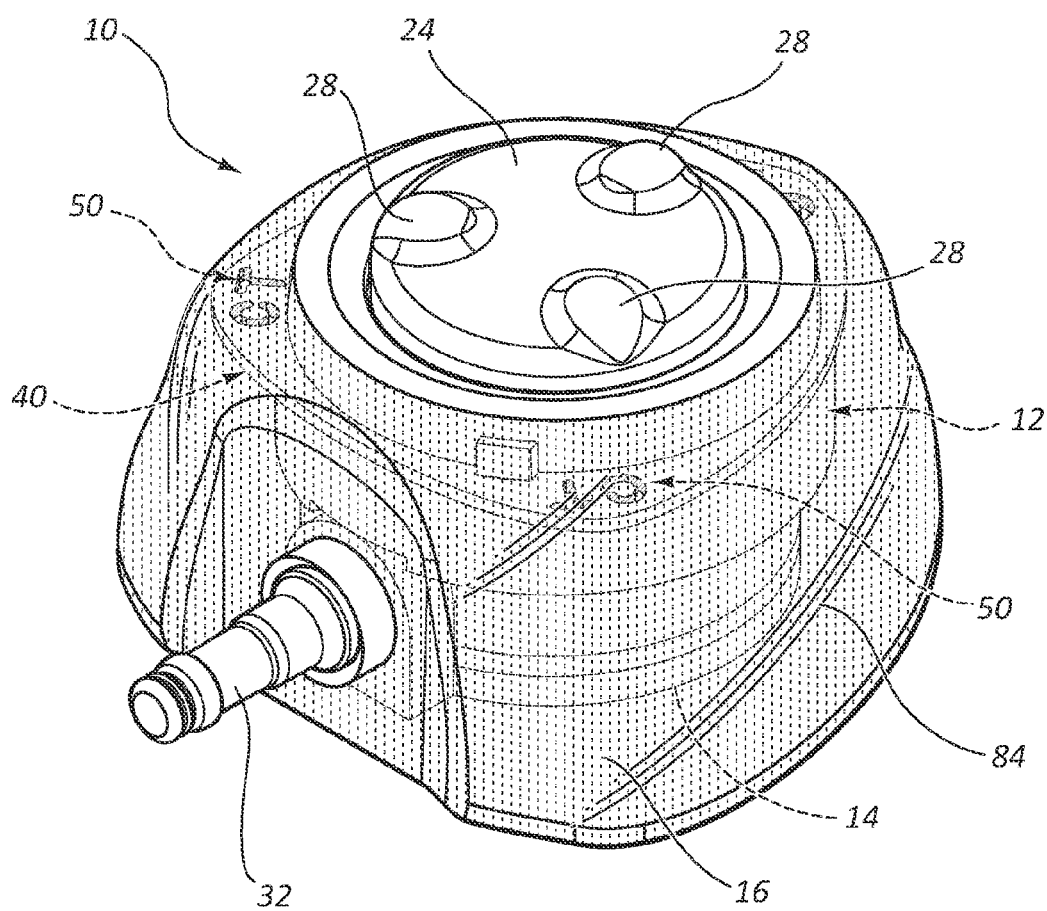
FIG. 8 is a perspective view of an implantable overmolded access port according to one embodiment.

FIG. 8 shows the port 10 according to one embodiment, wherein a colorant or other suitable opaque additive is included with the material that is used to form the outer cover 16, e.g., silicone, so as to render the outer cover opaque. In one embodiment, a colorant such as Kreative Color Purple, K-6050-13, provided by Kreative Liquid Color of Ontario, Calif., is intermixed with the silicone before the overmolding process, resulting in an opaque outer cover 16 for the port 10 after overmolding is complete. Of course, other materials and methods can be employed to render the outer cover opaque. Desired characteristics of the colorant or opaque additive in one embodiment include radiotranslucence, biocompatibility, and compatibility with the material from which the outer cover is made.

Figure 9:
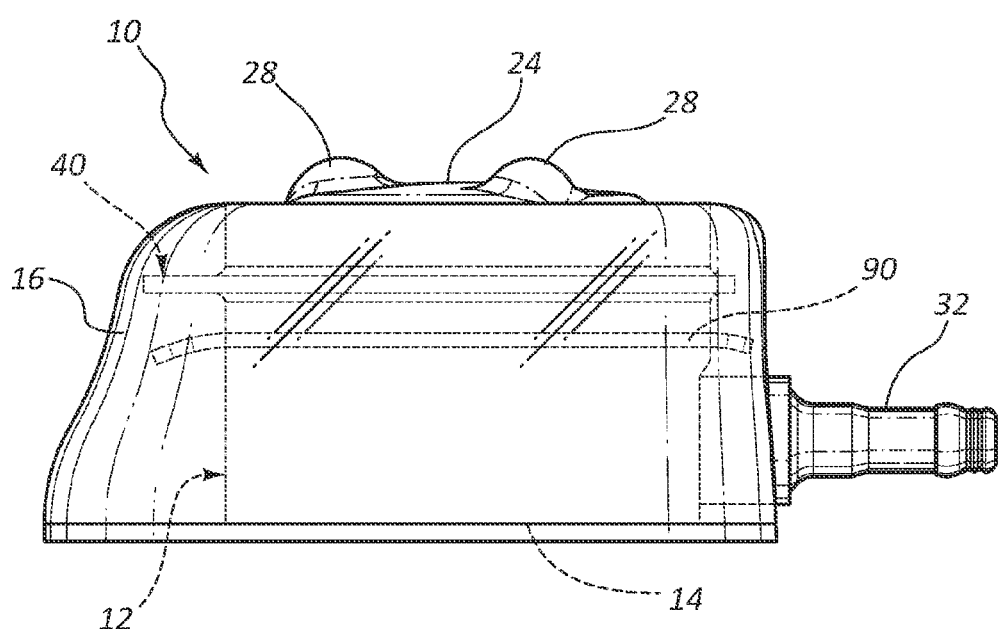
FIG. 9 is a cross sectional view of an implantable access port including an identification feature according to one embodiment.

FIG. 9 shows the port 10 according to another embodiment, wherein in addition to the flange 40, a secondary plate 90 is positioned below the flange as shown in FIG. 9. Like the flange 40, the plate 90 is covered by the outer cover 16 and in one embodiment includes through holes to serve as an anchoring feature for securing the engagement between the outer cover 16 and the internal body 12 of the port 10. Also like the flange 40, the plate 90 can include titanium, bismuth trioxide or other suitable material, or can differ in composition from the flange 40. Positioning of the plate 90 as shown in FIG. 9 limits visual observation of the indicia serving as identification features of the flange 40 to a top-looking-down point of view, as in FIGS. 1C and 3D.

Figure 10:
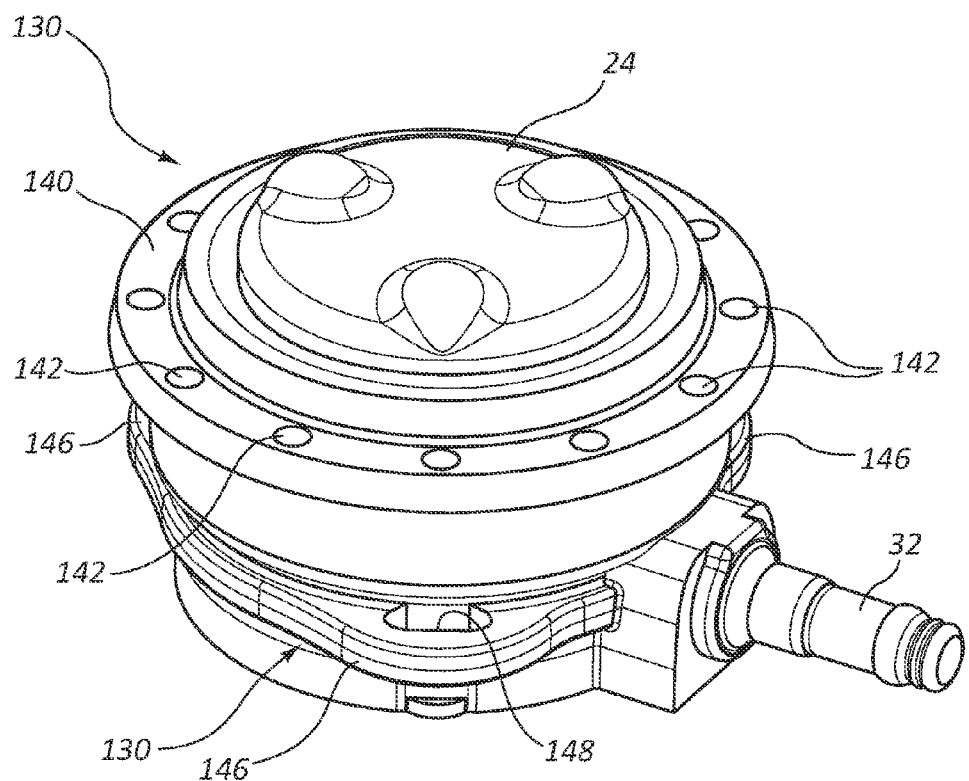
FIG. 10 is a perspective view of a body portion of an implantable access port including anchoring features according to one embodiment.
Figure 11:
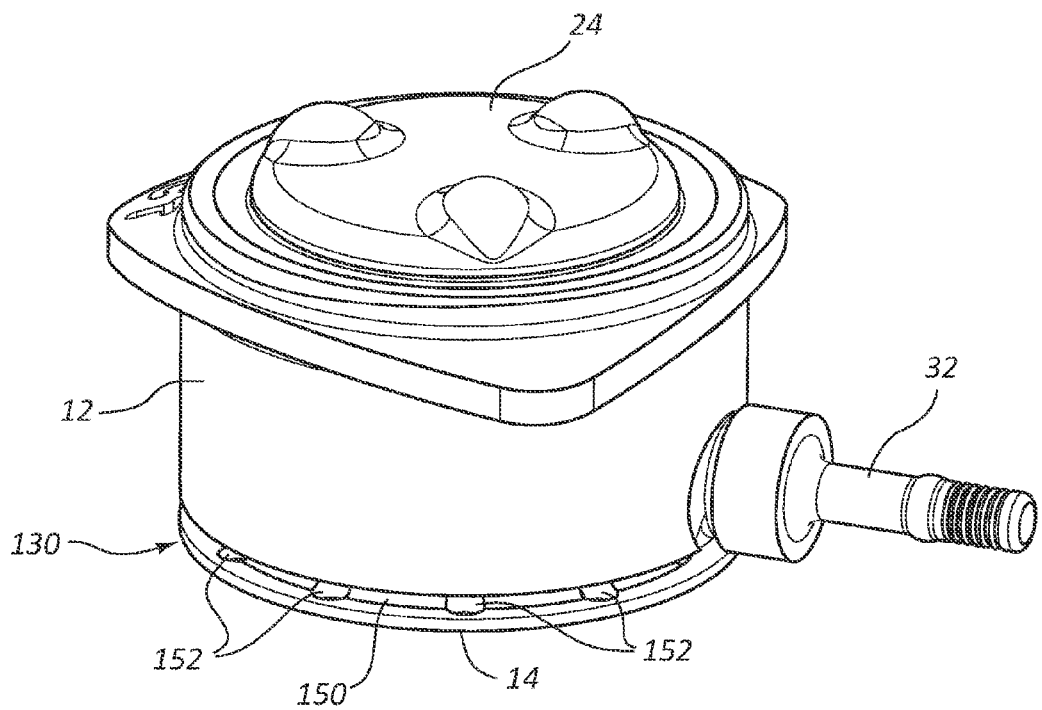
FIG. 11 is a perspective view of a body portion of an implantable access port including anchoring features according to one embodiment.
Figure 12:
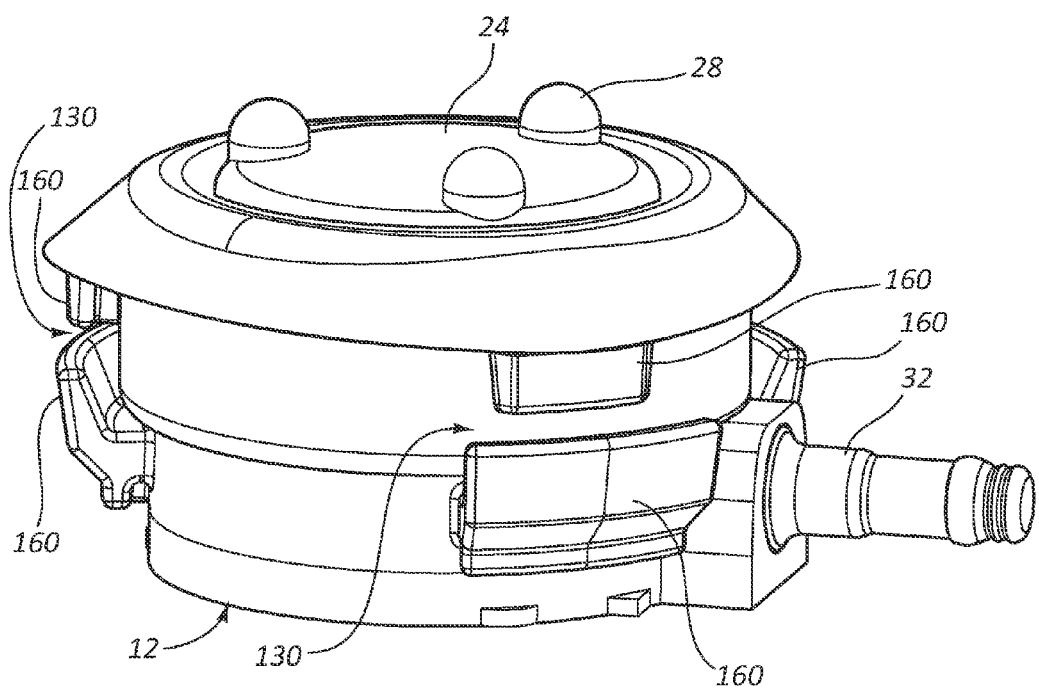
FIG. 12 is a perspective view of a body portion of an implantable access port including anchoring features according to one embodiment.

FIGS. 10-12 depict various embodiments disclosing additional examples of anchoring features for the internal body 12 of the port 10. The anchoring features to be described operate similar to the "CT" indicia cutouts and other anchoring features of the flange 40 described in the above embodiments in securing the overmolded outer cover to the internal port body.

In FIG. 10, anchoring features 130 are included on a flange 140 of the port body 12. The flange 140 is positioned circumferentially about and proximate to the septum 24 included on the port body 12. In particular, the anchoring features are implemented as a plurality of through holes 142 defined through the flange 140. In addition, one or more extensions 146 extend from the port body 12 below the flange 140 a sufficient distance to define additional through holes 148. As has been described relating to this and other embodiments herein including anchoring features, the silicone or other suitable material used to form the outer cover flows about the internal body 12 of the port during the overmolding process, passing through the anchoring features 130 to desirably enhance the adhesion of the outer cover to the port body.

FIG. 11 shows another example of an anchoring feature 130 for the port body 12, wherein an annular groove 150 is defined proximate the bottom 14 of the port body 12. A plurality of through holes 152 is defined in the groove so as to extend from the groove to the port body bottom surface 14 to enable flow therethrough of the outer cover material during the overmolding process.

FIG. 12 depicts yet another example of anchoring features 130, wherein a plurality of teeth 160 extends from surfaces of the port body 12. In particular, opposing pairs of teeth 160 are shown extending toward one another in FIG. 12, providing a gap not only between opposing teeth, but between the teeth and the adjacent side surface of the port body 12 so as to provide a suitable space through which the outer cover material can flow before solidifying after overmolding to anchor the outer cover to the port body. The size, shape, number, and position of the teeth can vary in a number of ways. More generally, it is appreciated that the preceding embodiments are merely examples of anchoring features and that other types and configurations of anchoring features can reside within the principles of the embodiments of the present invention.

Figure 13A:
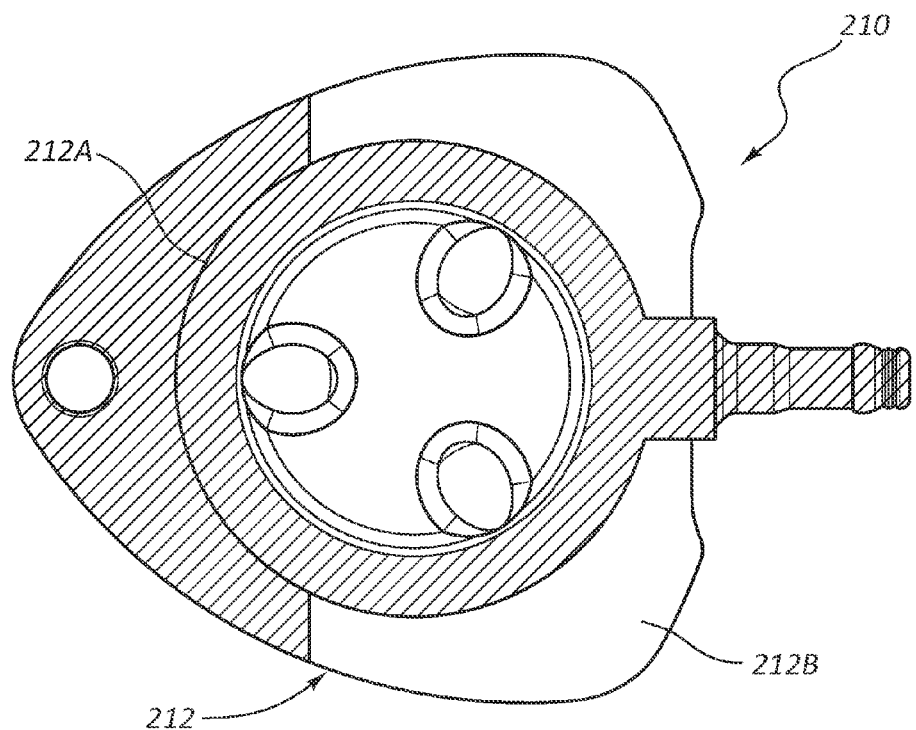
FIGS. 13A-13B are various views of an implantable access port including a complaint body portion according to one embodiment.
Figure 13B:
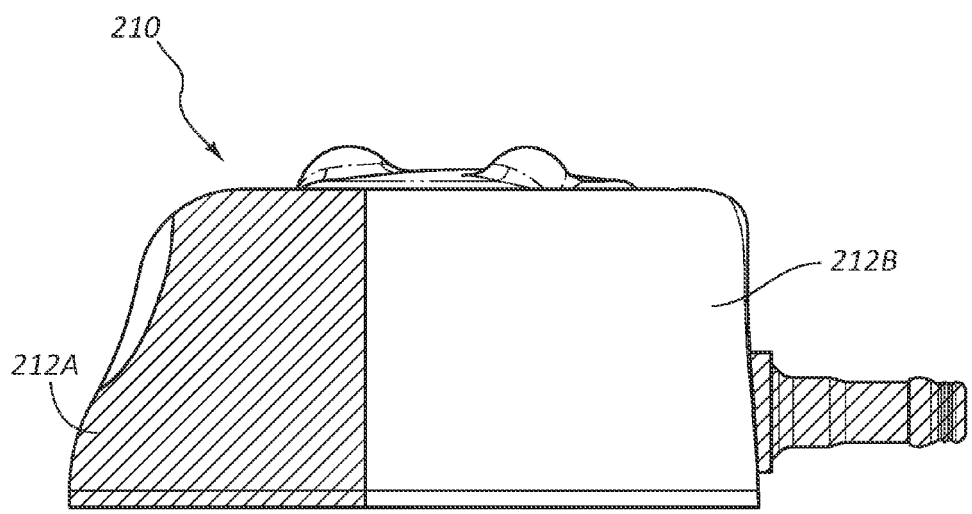

FIGS. 13A and 13B depict a port 210 according to one embodiment, wherein a body 212 of the port includes a first body portion 212A defining a nose of the body and a second body portion 212B defining the remaining portion of the body. In the present embodiment, the first body portion 212A includes a relatively rigid biocompatible material, such as acetyl resin or other thermoplastic, while the second body portion 212B includes a compliant overmolded material, such as silicone or other suitable biocompatible material. So configured, the port body nose defined by the first body portion 212A is relatively rigid to assist in placement of the port into a pocket defined in the tissue of the patient, while the remainder portion of the port body 212 defined by the second body portion 212B is compliant to increase patient comfort and to increase suturability of the port 210. Overmolding of the second body portion can be achieved in a manner similar to previous embodiments.

Figure 14A:
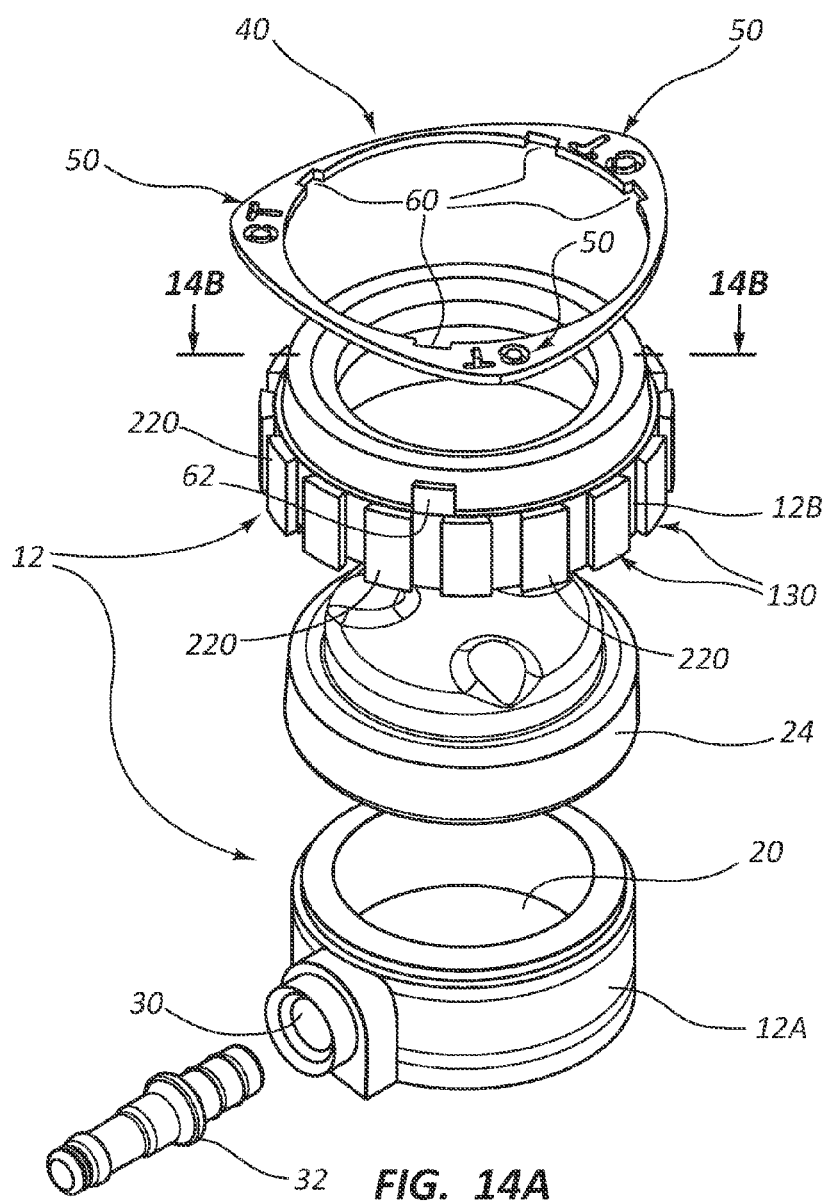
FIGS. 14A-14B are various views of an implantable access port body including anchoring features according to one embodiment.
Figure 14B:
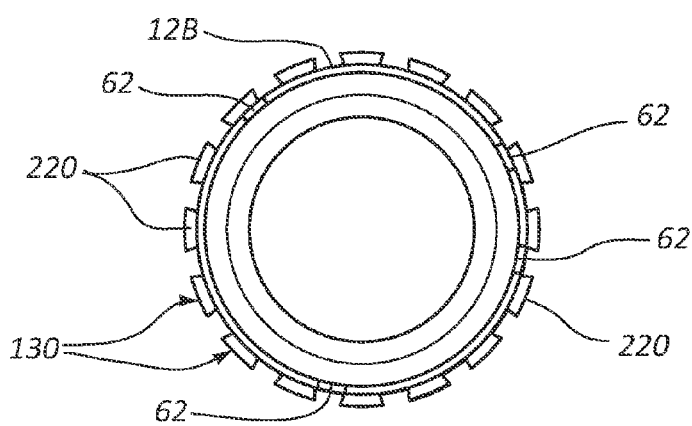

FIGS. 14A and 14B depict yet another example of anchoring features 130, wherein a plurality of dovetail extensions 220 extends from the circular side surface of the port body cap 12B about the circumference thereof. The dovetail extensions 220 provide ample surface area and entrapment areas between adjacent dovetails through which the outer cover material can flow before solidifying after overmolding to anchor the outer cover to the port body. The size, shape, number, position, and spacing of the dovetails teeth can vary in a number of ways. For instance, in addition to their inclusion on the port cap, the dovetail extensions could be included on the port base. Also, though shown extending about the entirety of the port cap circumference, in one embodiment the dovetail extensions could be defined only partially thereabout. These and other variations are contemplated.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An access port for providing subcutaneous access to a patient, comprising:
   a body defining a fluid cavity accessible via a septum;
   a compliant outer cover disposed about at least a portion of the body; and
   a flange independent from the body, the flange attached to the body proximate the septum, the flange including an identification feature observable via x-ray imaging technology, the identification feature conveying information indicative of at least one attribute of the access port.

2. The access port as defined in claim 1, wherein the flange extends about a perimeter of the body, wherein the identification feature includes a plurality of alphanumeric or symbolic characters, and wherein the identification feature indicates the access port is capable of power injection.

3. The access port as defined in claim 1, wherein the identification feature includes at least one hole defined through the flange so as to serve as an anchoring feature for securing the outer cover to the body.

4. The access port as defined in claim 1, wherein the flange includes a plurality of keyed notches that each fit over correspondingly keyed tabs on the body, and wherein the tabs are capable of being deformed after the notches are placed over the tabs such that the flange is retained by the body.

5. The access port as defined in claim 1, wherein the body of the access port includes acetyl resin, wherein the flange includes titanium, and wherein the flange impedes penetration of a needle a substantial distance into the outer cover.

6. An access port for providing subcutaneous access to a patient, comprising:
   a body defining a fluid cavity accessible via a septum, the body formed of a first material;
   a compliant outer cover disposed about at least a portion of the body; and
   a continuous annular flange attached to the body proximate the septum, the flange formed of a second material different from the first material, the flange and body being independent structures, the flange second material in contact with and covered by the outer cover, the flange impeding penetration of a needle past the flange within the outer cover when the needle is intended for penetration into the septum.

7. The access port as defined in claim 6, wherein the flange extends radially about a perimeter of the body, and wherein the flange further includes an anchoring feature for securing the outer cover to the body.

8. The access port as defined in claim 7, wherein the body includes a cap and a base, and the outer cover envelops the cap, the base, and the flange, the anchoring feature comprising a plurality of openings defined through the flange, a portion of the outer cover passing through the plurality of openings.

9. The access port as defined in claim 8, wherein the outer cover includes silicone, wherein the flange includes titanium, and wherein the plurality of openings define alphanumeric characters.

10. The access port as defined in claim 6, wherein the body includes an anchoring feature covered by the outer cover for securing the outer cover to the body, the anchoring feature including one of a plurality of teeth and a plurality of dovetail extensions extending from the body.

11. The access port as defined in claim 6, wherein the outer cover includes at least one of an antimicrobial component and an antithrombotic component.

12. The access port as defined in claim 6, wherein the body includes a cap bonded to a base, the septum captured between the cap and the base, the cap including a first keyed feature.

13. The access port as defined in claim 12, wherein the flange includes a second keyed feature corresponding to the first keyed feature of the cap to ensure correct orientation of the flange upon attachment to the cap.

14. An access port for providing subcutaneous access to a patient, comprising:
   a body including a cap and a base, the body defining a fluid cavity accessible via a septum;
   a compliant outer cover substantially covering the cap and the base to define an outer surface of the access port; and
   a flange separate from the body and attached to the cap proximate the septum, the flange including an identification feature observable via x-ray imaging technology, the identification feature conveying information indicative of at least one attribute of the access port.

15. The access port as defined in claim 14, wherein the flange further includes an anchoring feature for securing the outer cover to the body.

16. The access port as defined in claim 14, wherein the identification feature also functions as an anchoring feature for securing the outer cover to the body, and wherein the flange is positioned to impede penetration of a needle a substantial distance into the outer cover.

17. The access port as defined in claim 16, wherein the flange generally defines a triangular shape, and wherein the identification feature includes alphanumeric indicia disposed at each vertex of the flange.

18. The access port as defined in claim 17, wherein the alphanumeric indicia are defined as recessed features in the flange, and wherein the flange further comprises a plurality of through holes defined through the flange.

19. The access port as defined in claim 14, wherein the identification feature includes indicia defined through the flange, and wherein a compliant plug is disposed in the indicia so as to prevent visual observation of the indicia from at least one direction.

20. The access port as defined in claim 14, wherein the outer surface defined by the outer cover provides a suitable surface for application of coating thereon to inhibit at least one of microbe adhesion and thrombus formation.

21. An access port for providing subcutaneous access to a patient, comprising:
- a body defining a fluid cavity accessible via a septum;
- a compliant outer cover disposed about at least a portion of the body; and
- a flange separate from the body and attached to the body proximate the septum, the flange covered by the outer cover, the flange including an identification feature observable via x-ray imaging technology, the identification feature conveying information indicative of at least one attribute of the access port, wherein at least a portion of the outer cover is configured such that visual observation of the identification feature from at least one direction is prevented.

22. The access port as defined in claim 21, wherein the outer cover includes silicone, and wherein at least a portion of a surface of the outer cover is frosted so as to render the portion of the surface substantially opaque.

23. The access port as defined in claim 21, wherein the outer cover includes silicone mixed with a colorant so as to render the silicone opaque.

24. An access port for providing subcutaneous access to a patient, comprising:
- a body including a base and an attachable cap that cooperate to define a fluid cavity accessible via a septum; and
- a continuous annular flange formed from a radiopaque material, the flange attached to the cap proximate the septum to impede penetration of a needle distally beyond the flange, the body and the radiopaque material in contact with and substantially covered by a compliant outer cover.

* * * * *